(12) United States Patent
Gao et al.

(10) Patent No.: US 10,993,920 B2
(45) Date of Patent: May 4, 2021

(54) 2-DODECYL-6-METHOXYCYCLOHEXA-2,5-DIENE-1,4-DIONE AS A CANCER THERAPEUTIC

(71) Applicant: MIDDLE TENNESSEE STATE UNIVERSITY, Murfreesboro, TN (US)

(72) Inventors: Ying Gao, Murfreesboro, TN (US); Elliot Altman, Rockvale, TN (US)

(73) Assignee: Middle Tennessee State University, Murfreesboro, TN (US)

( * ) Notice: Subject to any disclaimer, the term of this patent is extended or adjusted under 35 U.S.C. 154(b) by 228 days.

(21) Appl. No.: 15/534,397

(22) PCT Filed: Dec. 9, 2015

(86) PCT No.: PCT/US2015/064785
§ 371 (c)(1),
(2) Date: Jun. 8, 2017

(87) PCT Pub. No.: WO2016/094554
PCT Pub. Date: Jun. 16, 2016

(65) Prior Publication Data
US 2017/0360722 A1      Dec. 21, 2017

Related U.S. Application Data

(60) Provisional application No. 62/089,578, filed on Dec. 9, 2014.

(51) Int. Cl.

| | |
|---|---|
| A61K 31/122 | (2006.01) |
| A61K 45/06 | (2006.01) |
| C07C 50/04 | (2006.01) |
| C07C 50/32 | (2006.01) |
| A61K 31/704 | (2006.01) |
| A61K 31/395 | (2006.01) |
| A61K 33/24 | (2019.01) |
| A23L 2/00 | (2006.01) |
| A61K 31/337 | (2006.01) |
| A61K 31/555 | (2006.01) |
| A23L 2/52 | (2006.01) |
| A23L 33/105 | (2016.01) |
| A23L 23/00 | (2016.01) |
| A23L 33/10 | (2016.01) |
| A23L 7/10 | (2016.01) |
| A61K 36/185 | (2006.01) |

(52) U.S. Cl.
CPC ............. *A61K 31/122* (2013.01); *A23L 2/00* (2013.01); *A23L 2/52* (2013.01); *A23L 7/10* (2016.08); *A23L 23/00* (2016.08); *A23L 33/10* (2016.08); *A23L 33/105* (2016.08); *A61K 31/337* (2013.01); *A61K 31/395* (2013.01); *A61K 31/555* (2013.01); *A61K 31/704* (2013.01); *A61K 33/24* (2013.01); *A61K 36/185* (2013.01); *A61K 45/06* (2013.01); *C07C 50/04* (2013.01); *C07C 50/32* (2013.01)

(58) Field of Classification Search
USPC ........................................................ 514/690
See application file for complete search history.

(56) References Cited

U.S. PATENT DOCUMENTS

| 2007/0248693 A1 | 10/2007 | Mazzio et al. |
| 2009/0004302 A1 | 1/2009 | Cyr |

FOREIGN PATENT DOCUMENTS

| CN | 103 948 004 A | 7/2014 |
| WO | WO 2014/059158 A1 | 7/2014 |

OTHER PUBLICATIONS

Abrams (New chemotherapeutic agents for breast cancer, Cancer, 1994, 1; 73(3 Suppl); pp. 1164-76 (abstract only)).*
Zheng (Effect of 2-dodecyl-6-methoxycyclohexa-2,5-diene-1,4-dione, isolated from *Averrhoa carambola* L. (Oxalidaceae) roots, on advanced glycation end-product-mediated renal injury in type 2 diabetic KKAy mice, Toxicology Letters 219 (2013) 77-84).*
Laere (NF-κB activation in inflammatory breast cancer is associated with oestrogen receptor downregulation, secondary to EGFR and/or ErbB2 overexpression and MAPK hyperactivation, British Journal of Cancer (2007) 97, 659-669).*
Acton et al., "Potential Prophylactic Antitumor Activity of Retinylidene 1,3-Diketones," *J. Med. Chem.*, 1980; 23(7):805-809.
Adams, "Proteasome inhibition in cancer: Development of PS-341," *Semin. Oncol.*, 2001; 28(6):613-619.
Ali et al., "Preliminary cytotoxic activity of different extracts of *Averrhoa bilimbi* (fruits)," *International Current Pharmaceutical Journal*, Feb. 2013; 2(3):83-84.
American Cancer Society, "Cancer Facts & Figures 2014," Atlanta: American Cancer Society; 2014.
Arshad et al., "Exploiting the cancer and diabetes metabolic connection for therapeutic purposes," 2013 IEEE International Workshop on Genomic Signal Processing and Statistics, Houston, TX, 2013, pp. 44-44.
Basu et al., "Crosstalk between extrinsic and intrinsic cell death pathways in pancreatic cancer: synergistic action of estrogen metabolite and ligands of death receptor family," *Cancer Res.*, 2006; 66(8):4309-4318.
Boatright et al., "Mechanisms of caspase activation," *Current Opin Cell Biol.*, 2003; 15:725-731.
Brondani et al., "Synthesis and antitumour activity of the Primin (2-methoxy-6-n-pentyl-1,4-benzoquinone) and analogues," *Med. Chem.*, 2007; 3:369-372.
Cain et al., "Apaf-1 oligomerizes into biologically active ~700-kDa and inactive ~1.4-MDa apoptosome complexes," *Journal of Biological Chemistry*, 2000; 275(9):6067-6070.

(Continued)

*Primary Examiner* — Kathrien A Cruz
(74) *Attorney, Agent, or Firm* — Mueting Raasch Group

(57) ABSTRACT

2-Dodecyl-6-methoxycyclohexa-2,5-diene-1,4-dione (DMDD), as well as variants, derivatives, analogs, modifications, and conjugates thereof, are identified as therapeutic agents for treating or preventing human cancers and precancerous conditions. DMDD can be isolated from the root of *Averrhoa carambola* L., commonly known as starfruit. Pharmaceutical and nutraceutical compositions, as well as dietary supplements, are provided, as are methods of administration and treatment.

9 Claims, 10 Drawing Sheets

(56) References Cited

OTHER PUBLICATIONS

Dazert, "mTOR signaling in disease," *Curr. Opin. Cell Biol.*, 2011; 23:744-755.
Dominguez et al., "Synthesis and Antimalarial Effects of Phenothiazine Inhibitors of a *Plasmodium falciparum* Cysteine Protease," *J. Med. Chem.*, 1997; 40:2726-2732.
Dowling et al., "Metformin inhibits mammalian target of rapamycin—dependent translation initiation in breast cancer cells," *Cancer Res.*, 2007; 67(22):10804-10812.
Gallagher et al., "Diabetes, cancer, and metformin: connections of metabolism and cell proliferation," *Ann. N.Y. Acad. Sci.*, 2011; 1243:54-68.
Galli et al., "Oxidative stress and reactive oxygen species," *Contrib. Nephrol.*, 2005; 149:240-60.
Gao et al., "The antidiabetic compound 2-Dodecyl-6-methoxycyclohexa-2,5-diene-1,4-dione, isolated from *Averrhoa carambola* L. demonstrates significant antitumor potential against human breast cancer cells," *Oncotarget*, Jun. 15, 2015; 6(27):24304-24319.
George et al., "New Biologically Active Compounds from 1,3-Diketones," *Res. J. Chem. Sci.*, 2011; 1(3):102-108.
Gilmore et al., "Inhibition of NF-κB signaling as a strategy in disease therapy," Current Topics Microbiology, 2011, 349: 245-263.
Hoesel et al., "The complexity of NF-κB signaling in inflammation and cancer," *Mol. Cancer*, Aug. 2, 2013; 12:86.
Hsu et al., "The mTOR-regulated phosphoproteome reveals a mechanism of mTORC1-mediated inhibition of growth factor signaling," *Science*, 2011; 332(6035): 1317-1322.
Huang et al., "Effects of *Averrhoa carambola* L. Root Polysaccharide on Serum Insulin and Index of Thymus, Spleen in STZ-induced Diabetic Mice," *Chin. Pharm.* 2009, 12, 848-50. (In Chinese with English Abstract).
Huang et al., "Effects of Alcoholic Extracts of *Averrhoa carambola* L. Root on Blood Glucose Level and Lipid Peroxidation in Diabetic Mice," *Lishizhen Med. Mater. Med. Res.* 2009; 20(11):2730-2731. (In Chinese with English Abstract).
Kluck et al., "The release of cytochrome c from mitochondria: a primary site for Bcl-2 regulation of apoptosis," *Science*, 1997; 275(5303):1132-1136.
Laplante et al., "mTOR signaling," *Cold Spring Harb. Perspect. Biol.*, 2012; 4:a011593.
Liao et al., "Association between diabetes mellitus and breast cancer risk: a meta-analysis of the literature," *Asian Pac. J. Cancer Prev.*, 2011; 12:1061-1065.
Lipscombe et al., "Diabetes mellitus and breast cancer: a retrospective population-based cohort study," *Breast Canc Res Treat*, Aug. 2006; 98:349-56.
Lipscombe et al., "Incidence of diabetes among postmenopausal breast cancer survivors," *Diabetologia*, Mar. 2013; Published Online: Dec. 13, 2012; 56(3):476-483.
Liu et al., "Proline oxidase activates both intrinsic and extrinsic pathways for apoptosis: the role of ROS/superoxides, NFAT and MEK/ERK signaling," *Oncogene*, 2006; 25(41):5640-5647.
Li-Weber, M. "Targeting apoptosis pathways in cancer by Chinese medicine." *Cancer Lett.* 2013; 332:304-312.
Mariani et al., "Oxidative stress in brain aging, neurodegenerative and vascular diseases: an overview," *J Chromatogr. B*, 2005; 827:65-75.
Matés et al., "Role of reactive oxygen species in apoptosis: implications for cancer therapy," *Int. J. Biochem. Cell Biol.*, 2000; 32:157-170.
Maussang et al., "Human cytomegalovirus-encoded chemokine receptor US28 promotes tumorigenesis," *Proc Natl Acad Sci USA*, 2006; 103(35):13068-13073.
Melo et al., "[First observations on the topical use of Primin, Plumbagin and Maytenin in patients with skin cancer]," *Rev. Inst. Antibiot. (Recife)*, 1974; 14(1-2):9-16. (In Portuguese with English Summary on p. 15).

Miller et al., "Identification of known drugs that act as inhibitors of NF-κB signaling and their mechanism of action," *Biochem. Pharmacol.*, 2010; 79(9):1272-1280.
Ozben, "Oxidative stress and apoptosis: impact on cancer therapy," *J Pharm Sci.*, 2007; 96(9):2181-2196.
Patient Information Sheet, "2-Methoxy-6-n-Pentyl-4-Benzoquinone (Primin)," *Chemotechnique Diagnostics, Dormer Laboratories Inc.*, Mar. 24, 2009; M-008-PS1, Issue 1.
Peairs et al., "Diabetes mellitus and breast cancer outcomes: a systematic review and meta-analysis," *J. Clin. Oncol.*, 2011; 29(1):40-6.
Petronzi et al., "Cyclohexa-2,5-diene-1,4-dione-based antiproliferative agents: design, synthesis, and cytotoxic evaluation," *J. Exp. Clin. Cancer*, 2013; 32:24-36.
Pham et al., "Effects of *Averrhoa carambola* L. (Oxalidaceae) juice mediated on hyperglycemia, hyperlipidemia, and its influence on regulatory protein expression in the injured kidneys of streptozotocin-induced diabetic mice" *Am. J. Transl. Res.*, 2017; 9(1):36-49.
PubChem Substance, SID 135171273; retrieved on Jan. 29, 2016, 6 pages.
PubChem Substance, SID 76736811; retrieved on Feb. 26, 2019; 5 pages.
PubChem Compound, CID 0193384; retrieved on Feb. 26, 2019; 15 pages.
Reuter et al., "Oxidative stress, inflammation, and cancer: how are they linked?" *Free Rad. Biol. Med.*, 2010; 49(11):1603-1616.
Roy et al., "Cross-talk in cell death signaling," *J. Ex. Med*, 2000; 192(8):F21-F25.
Sahra et al., "Metformin, independent of AMPK, induces mTOR inhibition and cell-cycle arrest through REDD1," *Cancer Res.*, 2011; 71(13):4366-4372.
Schmalle et al., "Structure of 6-dodecyl-2-methoxy-1,4-benzoquinone, a new synthetic contact allergen," *Acta Cryst. C.*, 1988; 44(Pt 4):693-5.
Sethi et al., "Potential pharmacological control of the NF-κB pathway," *Trends Pharmacol Sci.*, 2009; 30(6):313-321.
Sharma et al., "Synthesis and QSAR studies of pyrimido[4,5-d]pyrimidine-2,5-dione derivatives as potential antimicrobial agents," *Bioorg. Med. Chem. Lett.*, 2004; 14:4185-4190.
Singh et al., "Prophylactic Role of *Averrhoa carambola* (Star Fruit) Extract against Chemically Induced Hepatocellular Carcinoma in Swiss Albino Mice," *Adv Pharmacol Sci.*, 2014 (available online Feb. 19, 2014), Article ID 158936, 8 pages.
Sosa et al., "Oxidative stress and cancer: an overview," *Ageing Res.Rev.*, Jan. 2013 (published online Oct. 31, 2012); 12(1):376-390.
Susin et al., "Two distinct pathways leading to nuclear apoptosis," *J Exp Med.*, 2000; 192(4):571-58.
Tadros et al., "Pharmacognostical and biological study of the stem and leaf of *Averrhoa carambola* L. Grown in Egypt," *Bull. Fac. Pharm. Cairo Univ.*, 2004; 42(2):225-246.
Tait et al., "Mitochondria and cell death: outer membrane permeabilization and beyond," *Nat. Rev. Mol. Cell Biol.*, 2010; 11:621-632.
Veskoukis et al., "Dietary oxidative stress and antioxidant defense with an emphasis on plant extract administration," 2012; *Cell Stress and Chaperones*, 17:11-21.
Voboril et al., "Constitutive NF-κB activity in colorectal cancer cells: impact on radiation-induced NF-κB activity, radiosensitivity, and apoptosis," *Neoplasma*, 2006; 53(6):518-523.
Wen et al., "Study on the Chemical Constituents from *Averrhoa carambola* L. Root and Its Hypoglycemic Activities," *Pharmacy and Clinics of Chinese Materia Medica*, Feb. 2013; (In Chinese with English Abstract). Available online at http://www.dissertationtopic.net/doc/1814029.
Wen et al., "Isolation, Identification and Determination for Benzoquinone Compounds from *Averrhoa carambola* Root," *Chinese Journal of Experimental Traditional Medical Formulae*, Jun. 2014; 20(11):70-4. (In Chinese with English Abstract).
Xu et al., "Protective Effects of Total Extracts of *Averrhoa carambola* L. (Oxalidaceae) Roots on Streptozotocin-Induced Diabetic Mice," *Cell. Physiol. Biochem*, 2014 (published online Apr. 28, 2014); 33:1272-1282.

(56) References Cited

OTHER PUBLICATIONS

Yamamoto et al., "Therapeutic potential of inhibition of the NF-κB pathway in the treatment of inflammation and cancer," *J. Clin. Invest.*, 2011; 107(2): 135-142.

Ye et al., "Role of reactive oxygen species and p53 in chromium(VI)-induced apoptosis," *J. Biol. Chem.*, 1999; 274(49):34974-34980.

Zheng et al., "Effect of 2-dodecyl-6-methoxycyclohexa-2,5-diene-1,4-dione, isolated from *Averrhoa carambola* L. (Oxalidaceae) roots, on advanced glycation end-product-mediated renal injury in type 2 diabetic KKAy mice," *Toxicol Lett.*, 2013 (available online Mar. 13, 2013); 219(1):77-84.

Zoncu et al. "mTOR: from growth signal integration to cancer, diabetes and ageing," *Nature Rev. Mol. Cell Biol.*, 2011; 12(1):21-35.

Zorov et al., "Mitochondrial ROS-induced ROS release: an update and review," *Biochim. Biophys. Acta.*, 2006; 1757(5-6):509-517.

International Search Report and Written Opinion for International Patent Application No. PCT/US2015/064785, dated Feb. 26, 2016; 11 pages.

International Preliminary Report on Patentability for International Patent Application No. PCT/US2015/064785, dated Jun. 22, 2017; 9 pages.

Hua et al., "Mechanisms for estrogen receptor expression in human cancer," *Exp Hematol Oncol*, 2018; 7:24. 11 pages.

Silberstein and Daniel, "Reversible Inhibition of Mammary Gland Growth by Transforming Growth Factor-β," *Science*, 1987 237(4812):291-3.

\* cited by examiner

A 2-dodecyl-6-methoxycyclohexa-2,5-diene-1,4-dione (DMDD)

B

A (cont'd)

2-DODECYL-6-METHOXYCYCLOHEXA-2,5-DIENE-1,4-DIONE AS A CANCER THERAPEUTIC

This application is the § 371 U.S. National Stage of International Application No. PCT/US2015/064785, filed Dec. 9, 2015, which claims the benefit of U.S. Provisional Application Serial No. 62/089,578, filed Dec. 9, 2014, each of which is incorporated herein by reference in its entirety.

BACKGROUND

Human cancers are the most common cause of death in the world, and breast cancer has the highest mortality in women. It is estimated that 463,540 new cases of breast cancer were diagnosed in the US in 2013 and 200,540 of those people died (American Cancer Society. Cancer Facts & FIGS. 2014. Atlanta: American Cancer Society; 2014). Current therapeutic treatments for cancer usually cause serious side effects, such as bladder, kidney, lung, or heart damage. The development of effective drugs with fewer adverse side effects for the chemopreventive intervention of cancers is thus a top priority in cancer research.

*Averrhoa carambola L.* (family Oxalidaceae) is a perennial herb widely distributed in Southeast Asia. Its roots have been employed in Traditional Chinese Medicine (TCM) for thousands of years as a remedy for arthralgia and chronic paroxysmal headaches. A cyclohexanedione, 2-dodecyl-6-methoxycyclohexa-2,5-diene-1,4-dione (DMDD), was isolated from the roots of *Averrhoa carambola L.* and found to exhibit hypoglycemic and anti-lipid peroxidative effects in diabetic mice. Huang et al., *Chin. Pharm.* 2009, 12, 848-850; Huang et al., *Lishizhen Med. Mater. Med. Res.* 2009, 20, 2730-2731; Zheng et al., 2013, *Toxicology letters*, 219 (1), 77-84.

SUMMARY OF THE INVENTION

The invention identifies 2-dodecyl-6-methoxycyclohexa-2,5-diene-1,4-dione (DMDD), including variants, derivatives, analogs, modifications, and conjugates thereof, as a therapeutic agent for treating human cancers. In one aspect, the disclosure provides a method for treating or preventing cancer or a precancerous condition in a subject by administering to the subject a composition that includes an effective amount of 2-dodecyl-6-methoxycyclohexa-2,5-diene-1,4-dione (DMDD), or a variant, derivative, analog, modification, or conjugate thereof, as described herein. The cancer can be bone cancer, brain cancer, breast cancer, ovarian cancer, cervical cancer, cancer of the larynx, lung cancer, esophageal cancer, pancreatic cancer, prostate cancer, testicular cancer, skin cancer, cancer of the spine, stomach cancer, colon cancer, bladder cancer, kidney cancer, uterine cancer, thyroid cancer, a blood cancer, or a cancer of the immune system, without limitation. The subject may be suffering from cancer or a precancerous condition, or may have a risk factor for developing cancer or a precancerous condition, such that DMDD or a variant, derivative, analog, modification, or conjugate thereof can be administered prior to the development of a cancer or precancerous condition.

In another aspect, the disclosure provides a method for inhibiting the growth of a tumor in a subject by administering to the subject a composition that includes an effective amount of 2-dodecyl-6-methoxycyclohexa-2,5-diene-1,4-dione (DMDD), or variant, derivative, analog, modification, or conjugate thereof as described herein. The tumor can be a solid tumor disposed in the bone, brain, breast, ovary, cervix, larynx, lung, esophagus, pancreas, prostate, testicle, skin, spine, stomach, colon, bladder, kidney, uterus, or thyroid of the subject, without limitation.

The subject to whom DMDD, or variant, derivative, analog, modification, or conjugate thereof, is administered may additionally suffer from diabetes, prediabetes, metabolic syndrome, or other medical condition.

The composition may include an extract prepared from the roots of *Averrhoa carambola L*, and may further include one or more of a pharmaceutically acceptable carrier or a second therapeutic agent. The second therapeutic agent can be a cytokine, a chemokine, a therapeutic antibody, an adjuvant, an antioxidant, or a chemotherapeutic agent, without limitation. A preferred second therapeutic agent is a chemotherapeutic drug for the treatment or prevention of breast cancer.

Also provided by the disclosure is 2-dodecyl-6-methoxycyclohexa-2,5-diene-1,4-dione (DMDD), or variant, derivative, analog, modification, or conjugate thereof, for use in the treatment or prevention of cancer or a precancerous condition, or for use in inhibiting the growth of a tumor.

Also provided by the disclosure is 2-dodecyl-6-methoxycyclohexa-2,5-diene-1,4-dione (DMDD), or variant, derivative, analog, modification, or conjugate thereof, for use in the preparation of a medicament for the treatment or prevention of cancer or a precancerous condition, or for inhibiting the growth of a tumor.

Also provided by the disclosure is a plant extract that includes 2-dodecyl-6-methoxycyclohexa-2,5-diene-1,4-dione (DMDD), or variant, derivative, analog, modification, or conjugate thereof, for use in the treatment or prevention of cancer or a precancerous condition, or for use in inhibiting the growth of a tumor.

Also provided by the disclosure is a plant extract comprising 2-dodecyl-6-methoxycyclohexa-2,5-diene-1,4-dione (DMDD), or variant, derivative, analog, modification, or conjugate thereof, for use in the preparation of a medicament for the treatment or prevention of cancer or a precancerous condition, or for inhibiting the growth of a tumor.

The plant extract is preferably from the plant *Averrhoa carambola*, more specifically *Averrhoa carambola L.*, and is preferably in the form of a root extract.

Pharmaceutical compositions are also provided by the disclosure. In one embodiment, a pharmaceutical composition may include a first therapeutic agent comprising 2-dodecyl-6-methoxycyclohexa-2,5-diene-1,4-dione (DMDD), or variant, derivative, analog, modification, or conjugate thereof, and a pharmaceutically acceptable carrier. Optionally, at least one second therapeutic agent is included, such as, without limitation, doxorubicin (Adriamycin®), epirubicin (Ellence®), paclitaxel (Taxol®) docetaxel (Taxotere®), fluorouracil (5-FU), cyclophosphamide (Cytoxan®), trastuzumab (Herceptin®), Pertuzumab (Perjeta®), methotrexate, cisplatin, carboplatin, vinorelbine (Navelbine®), Capecitabine (Xeloda®), liposomal doxorubicin (Doxil®), gemcitabine (Gemzar®), mitoxantrone, ixabepilone (Ixempra®), albumin-bound paclitaxel (nab-paclitaxel or Abraxane®) and Eribulin (Halaven®). Alternatively or additionally, a third therapeutic agent is optionally included, which can be, without limitation, a cytokine, a chemokine, a therapeutic antibody, an adjuvant, and an antioxidant. The pharmaceutical composition can contain one or more first therapeutic agent(s), one or more first and second therapeutic agents, one or more first and third therapeutic agents, or one or more first, second and third therapeutic agents.

Also provided by the disclosure is a dietary supplement that includes 2-dodecyl-6-methoxycyclohexa-2,5-diene-1,4-dione (DMDD), or variant, derivative, analog, modification, or conjugate thereof.

Also provided by the disclosure is a nutraceutical composition comprising 2-dodecyl-6-methoxycyclohexa-2,5-diene-1,4-dione (DMDD), or variant, derivative, analog, modification, or conjugate thereof. Exemplary nutraceutical compositions include, without limitation, cereals, beverages and soups.

It should be understood that embodiments of the invention described herein with reference to 2-dodecyl-6-methoxycyclohexa-2,5-diene-1,4-dione (DMDD) are equally applicable to variants, derivatives, analogs, modifications, and conjugates of DMDD, and further that these variants, derivatives, analogs, modifications, and conjugates of DMDD can be substituted for DMDD in any or all embodiments of the invention.

DESCRIPTION OF ILLUSTRATIVE EMBODIMENTS

Figure 1:
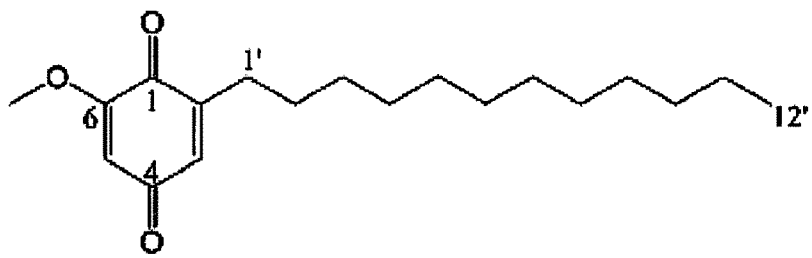
FIG. 1 shows the structure of 2-dodecyl-6-methoxycyclohexa-2,5-diene-1,4-dione (DMDD) and the effect of different concentrations of DMDD on cell viability. A, Chemical structure of DMDD. B, $IC_{50}$ (μM) values of DMDD in human breast carcinoma cell lines (MCF-7 and BT20) and the normal cell line (HMEC) in vitro. Different concentrations of DMDD were used to treat the cells for 48 h and cell viability was assessed using a PrestoBlue fluorescence assay. Values are means±SD of three independent experiments.
Figure 1:
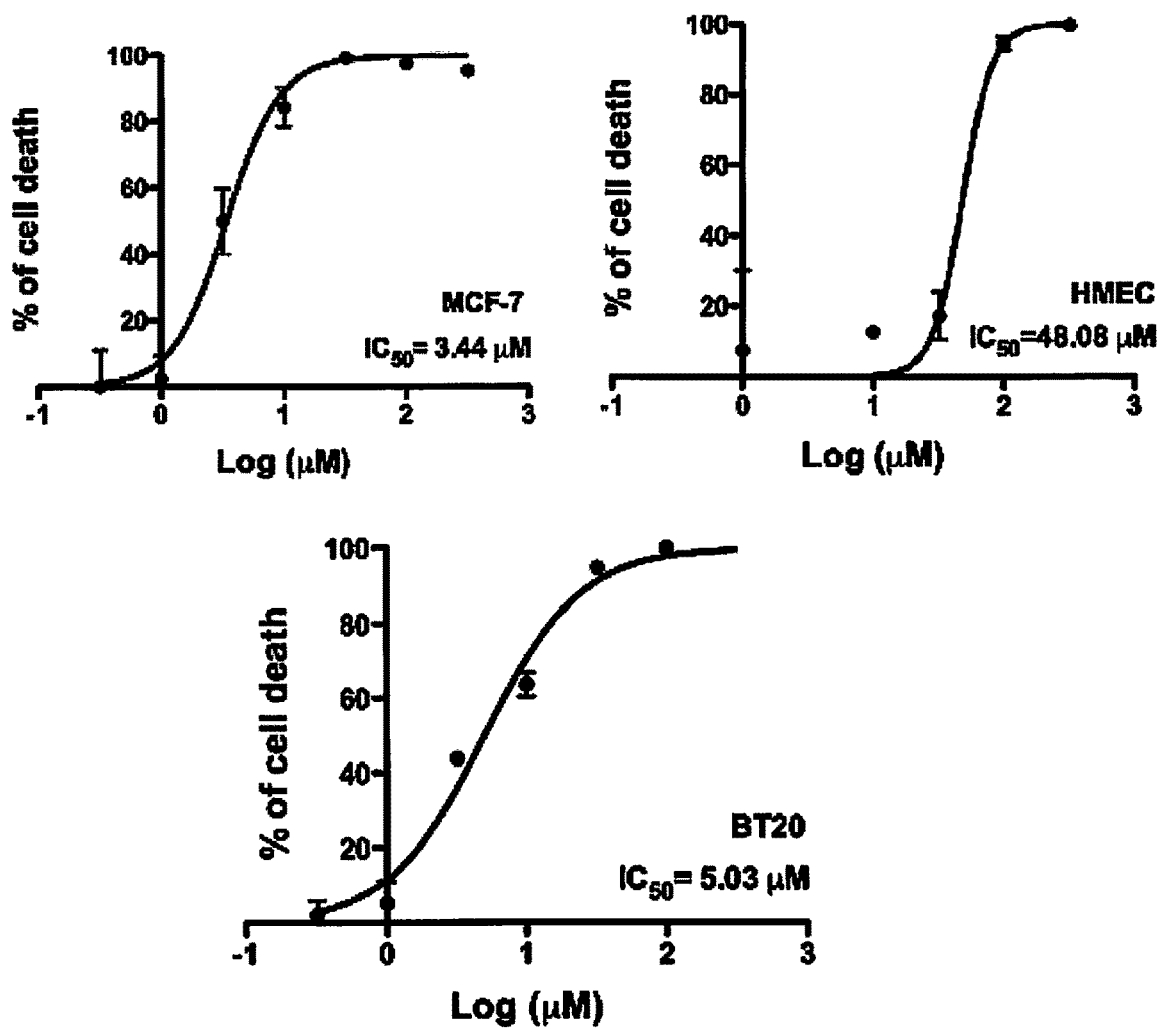

The present disclosure provides compounds, compositions and methods relating to the p-benzoquinone derivative, 2-dodecyl-6-methoxycyclohexa-2,5-diene-1,4-dione (DMDD), including variants, derivatives, analogs, modifications, or conjugate thereof, as well as its use as a prophylactic or therapeutic agent, for example, to prevent or treat cancers, precancerous conditions, or growth of tumors. Other names for DMDD include 2-dodecyl-6-methoxy-cyclohexa-2,5-diene-1,4-dione; 2-dodecyl-6-methoxy-p-benzoquinone; 6-dodecyl-2-methoxy-1,4-benzoquinone; 2-dodecyl-6-methoxy-2,5-cyclohexadiene-1,4-dione; 2-lauryl-6-methoxy-p-benzoquinone; CAS No. 4075-01-8; and 6-DMBQ (PubChem). Some references to DMDD may describe it as "2-methoxy-6-dodecyl" instead of "2-dodecyl-6-methoxy" due to the symmetry of the p-benzoquinone ring structure. The structure of DMDD was described by Schmalle et al. (Acta Crystallogr. Section C, Crystal Struct. Comm. 44(Pt 4):1988 pr 15, pp. 693-695), and is also described in the PubChem Substance (e.g., SID 76736811) and Compound (e.g., CID 193384) Databases. See also ChemSpider, CSID:167812, http://www.chemspider.com/Chemical-Structure.167812.html (accessed 20:44, Nov. 10, 2014).

DMDD is a cyclohexanedione having the following structure:

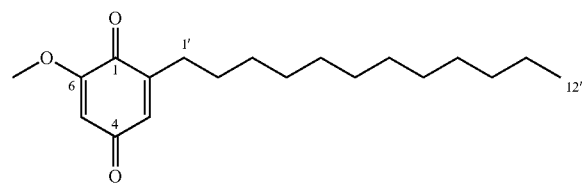

2-dodecyl-6-methoxycyclohexa-2,5-diene-1,4-dione (DMDD)

Variants, derivatives or modifications of DMDD encompassed by the disclosure include, for example, 2-alkyl-6-methoxycyclohexa-2,5-diene-1,4-diones having an alkyl group at the C-2 ring position that can vary in length; for example, the 2-alkyl group can contain 18, 17, 16, 15, 14, 13, 12 (2-dodecyl, DMDD), 11, 10, 9, 8, 7, 6, 5 (e.g., primin), or fewer carbon atoms. More generally, the alkyl group can be positioned at any available ring carbon; for example, referring to the structure shown above, the alkyl group in various DMDD derivatives encompassed by the disclosure can be positioned at C-2, C-3 or C-5. The benzoquinone is substituted with alkoxy. Exemplary alkoxy groups include but are not limited to ethoxy or methoxy; preferably the alkyoxy group is methoxy. The alkyoxy group is preferably at the C-6 ring position (6-alkoxy), although it can be positioned at any available ring carbon; for example, in the structure shown above, it could be positioned at C-3, C-5 or C-6. In some embodiments of a DMDD variant or derivative, the alkoxy group is meta to the alkyl group; in some embodiments the alkoxy group is para to the alkoxy group; and in some embodiment the alkoxy group is ortho to the alkyl group. Optionally, one or both of the available ring carbons (for example, the methines at positions C-3 and C-5 in the above structure) can be derivatized with a functional group of interest. For example, in some embodiments, the DMDD derivative or variant can include, as additional ring substituents, a second alkyl group and/or a second alkyoxy group. DMDD and its variants and derivatives described above are substituted benzoquinones having a 1,4 (para) or 1,2 (ortho) diketone structure. However, a substituted cyclic diketone having a 1,3 (meta) diketone structure is also encompassed by the disclosure. Preferred embodiments of variants, derivatives, modifications, analogs and/or conjugates of DMDD are those which are non-naturally occurring; other embodiments of variants, derivatives, modifications, analogs and/or conjugates of DMDD may be naturally occurring.

DMDD can be obtained from natural sources, or it can be chemically or enzymatically synthesized. A natural source for DMDD is from the Oxalidaceae family, genus *Averrhoa*, species *Averrhoa carambola*, more particularly *Averrhoa carambola L.*, commonly known as starfruit. The genus *Averrhoa* also includes *Averrhoa bilimbi* (tree cucumber). While plant parts such as wood, seeds, leaves, stems, fruit or flowers, may contain DMDD, DMDD is preferably obtained from plant roots, particularly the roots of *Averrhoa carambola L.* A root extract that contains DMDD can be readily prepared, and DMDD can be optionally isolated and/or purified from some or all of the other components of the root extract.

DMDD is a small organic molecule amenable to chemical synthesis. For example, the synthetic methods described in Petronzi et al. (J. Exp Clin. Cancer, 2013, 32:24-36) which utilized HU-331, a quinone anticarcinogenic drug synthesized from cannabidiol, as a starting material for synthesis of various cyclohexa-2,5-diene-1,4-diones, can be adapted to synthesize DMDD or its derivatives, variants or conjugates. It is also expected that DMDD can be enzymatically synthesized, either in vitro or in a microbial system, by isolating and employing the appropriate plant enzymes or their microbial analogs.

The compositions and methods of the invention may include or utilize purified or partially purified forms of DMDD, as well as crude plant extracts, preferably root extracts, that contain DMDD.

Therapeutic and Prophylactic Methods

DMDD has been shown by others to exhibit hypoglycemic and anti-lipid peroxidative effects in diabetic mice, but the efficacy of DMDD against cancer cell lines was unknown prior to the present work. Example 1 demonstrates that DMDD has significant anti-cancer activity. DMDD can therefore be used, or formulated for use, as a therapeutic or prophylactic agent to treat or prevent a cancer or a precancerous condition, or to arrest or inhibit the growth of a tumor. Likewise, DMDD can be used in the preparation of a medicament for the treatment or prevention of a cancer or a precancerous condition, or for inhibiting the growth of a tumor. Administration of DMDD to a subject in need thereof can occur before, during, or after the development of cancer or a precancerous condition.

DMDD can thus be administered therapeutically, to treat a subject suffering from a cancer or a precancerous condition. DMDD can be administered to inhibit the growth of a cancer or a tumor, malignant or benign, in a subject. Treatment is deemed therapeutic when it is initiated after the development of cancer, a precancerous condition, a tumor, or any other disease. Treatment initiated after the development of cancer may result in decreasing the severity of the symptoms of one of the conditions, or completely removing the symptoms.

DMDD can also be administered prophylactically, to prevent or delay the development of cancer or a precancerous condition in a subject. Treatment that is prophylactic, for instance, can be initiated before a subject develops cancer or manifests cancer symptoms. An example of a subject that is at known risk of developing cancer is a person having a risk factor, such as a genetic marker, that is associated with the disease. Examples of genetic markers indicating a subject has a predisposition to develop certain cancers include alterations in the BRAC1 and/or BRAC2 genes (breast, prostate, or colon cancer) and HPC1 (prostate cancer).

The method of the invention can be used to treat a variety of cancerous or precancerous conditions, including tumors or dysplasia. Cancers that can be treated include without limitation cancers of the bone, brain, breast, ovary, cervix, larynx, lung, esophagus, pancreas, prostate, testicle, skin, spine, stomach, colon, bladder, kidney, uterus, thyroid, blood, and immune system. A blood cancer can include leukemia. Preferably, the cancer being treated or prevented is a breast cancer. A tumor can be a solid tumor, such as a carcinoma, a sarcoma, or a lymphoma, and can be present, for example, in the bone, brain, breast, ovary, cervix, larynx, lung, esophagus, pancreas, prostate, testicle, skin, spine, stomach, colon, bladder, kidney, uterus, or thyroid, without limitation. The tumor may include a tumor of the immune system, such as a lymphoma. The tumor can made up of tumor cells, including lymphoid and myeloid cancers; multiple myeloma; cancers of the bone, brain, breast, ovary, cervix, larynx, lung, esophagus, pancreas, prostate, testicle, skin, spine, stomach, colon, bladder, kidney, uterus and thyroid, for example melanoma, head and neck squamous cell carcinoma, ovarian carcinoma, or cervical carcinoma.

A precancerous condition can be a carcinoma in situ or an in situ neoplasm such as, in the case of breast tissue, a ductal carcinoma in situ or a lobular carcinoma in situ. A precancerous condition can be a dysplasia or a hyperplasia, such as an atypical hyperplasia, including atypical ductal hyperplasia or atypical lobular hyperplasia. A dysplasia or hyperplasia can occur in any tissue or organ; for example, a dysplasia can be an epithelial dysplasia.

DMDD can be administered to a subject, preferably a human, having both cancerous or precancerous condition, and a diabetes-related condition such as diabetes, prediabetes and/or metabolic syndrome. DMDD can be administered to a subject having cancer-related diabetes. The diabetes can be Type I or Type II diabetes. Veterinary uses, including administration to domestic animals such as dogs and cats, are also contemplated.

Pharmaceutical Compositions

The present disclosure also provides a pharmaceutical composition that includes, as an active agent, DMDD, or a modification, derivative, variant or conjugate thereof, and a pharmaceutically acceptable carrier. The DMDD can be purified or partially purified, or it may be supplied as a plant extract.

The pharmaceutically acceptable carrier can include, without limitation, an excipient, a diluent, a solvent, an accessory ingredient, a stabilizer, a protein carrier, or other biological compound. Nonlimiting examples of suitable protein or biological carriers include keyhole limpet hemocyanin (KLH), ovalbumin, glycosaminoglycan, proteoglycan, and serum albumin, e.g., bovine serum albumin (BSA) or human serum albumin (HSA). The carrier can be a synthetic compound, such as dimethyl sulfoxide or a synthetic polymer, such as a polyalkyleneglycol, for example polyethelyene glycol. In a preferred embodiment, the pharmaceutically acceptable carrier includes at least one compound that is not naturally occurring or a product of nature.

In some embodiments, the active agent DMDD, or modification, derivative, variant or conjugate thereof, is formulated in combination with one or more additional active agents, such an anticancer, antiangiogenic, immunostimulatory or chemotherapeutic compound. Any known therapeutic agent can be included as additional active agent. The action of the additional active agent in the combination therapy can be cumulative to DMDD or it can be complementary, for example to manage side effects or other aspects of the patient's medical condition. The additional therapeutic agent(s) can be naturally occurring, or non-naturally occurring. In a preferred embodiment, the combination therapy includes at least one compound that is not naturally occurring or a product of nature.

Examples of additional therapeutic agents that can be included in the pharmaceutical composition include, without limitation, an immunostimulant, an antigen, a cytokine, a chemokine, an interferon, a therapeutic antibody, an adjuvant, an antioxidant, or a chemotherapeutic agent. Examples include an interferon such as IFN-$\alpha$, IFN-$\beta$, or IFN-$\gamma$ or a chemokine such as MIP-$1\alpha$, MIP-$1\beta$, MCP, RANTES or IP-10), a Toll-like receptor (TLR), or TLR adaptor molecule, or a cytokine such as interleukin-12 (IL-12), granulocyte-macrophage colony-stimulating factor (GM-CSF), interleukin-6 (IL-6), interleukin-18 (IL-18) and tumor necrosis factor (TNF); Toll like receptor (TLR1-9) and adaptor molecules (TRIF, Myd88, etc.). DMDD can generally be used in combination with any other general anticancer drug or any anticancer drug that is specific for a cancer such as breast cancer or ovarian cancer. Additional therapeutic agents that can be included in a pharmaceutical composition include treatment agents for diabetes, such as metformin.

The active agent is formulated as a pharmaceutical composition and then, in accordance with the method of the invention, administered to a mammal, such as a human patient, in any of a variety of forms adapted to the chosen route of administration. The formulations include those suitable for oral, rectal, vaginal, topical, nasal, ophthalmic or parental (including subcutaneous, intramuscular, intraperitoneal, intratumoral, and intravenous) administration.

The formulations may be conveniently presented in unit dosage form and may be prepared by any of the methods well-known in the art of pharmacy. In general, the formulations are prepared by uniformly and intimately bringing the active compound into association with a liquid carrier, a finely divided solid carrier, or both, and then, if necessary, shaping the product into the desired formulations.

Formulations suitable for oral administration can be presented as discrete units such as tablets, troches, capsules, lozenges, wafers, or cachets, each containing a predetermined amount of the active agent as a powder or granules, as liposomes, or as a solution or suspension in an aqueous liquor or non-aqueous liquid such as a syrup, an elixir, an emulsion, or a draught. The tablets, troches, pills, capsules, and the like can also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it can further contain a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, sugar, and the like. A syrup or elixir can contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent can be incorporated into sustained-release preparations and devices.

Formulations suitable for parenteral administration conveniently include a sterile aqueous preparation of the active agent, or dispersions of sterile powders of the active agent, which are preferably isotonic with the blood of the recipient. Parenteral administration of DMDD (e.g., through an I.V. drip) is one form of administration. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration can be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

Administration of DMDD

The active agent DMDD and synthetic derivatives thereof can be administered to a subject alone or in a pharmaceutical composition that includes the active agent and a pharmaceutically acceptable carrier. The active agent is administered to a patient, preferably a mammal, and more preferably a human, in an amount effective to produce the desired effect. DMDD can be administered in a variety of routes, including orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. DMDD can be introduced into the subject either systemically or at the site of a cancer or tumor.

The formulations can be administered as a single dose or in multiple doses. Useful dosages of the active agents can be determined by comparing their in vitro activity and the in vivo activity in animal models. Methods for extrapolation of effective dosages in mice, and other animals, to humans are known in the art.

Dosage levels of the active agent, including but not limited to DMDD, in the pharmaceutical compositions can be varied so as to obtain an amount of the active agent which is effective to achieve the desired therapeutic response for a particular subject, composition, and mode of administration, without being toxic to the subject. The selected dosage level will depend upon a variety of factors including the activity of the particular compound employed, or the ester, salt or amide thereof, the route of administration, the time of administration, the rate of excretion of the particular compound being employed, the duration of the treatment, other drugs, compounds and/or materials used in combination with the DMDD, the age, sex, weight, condition, general health and prior medical history of the subject being treated, and like factors well known in the medical arts.

Dosages and dosing regimens suitable for therapeutic or prophylactic administration of DMDD can be readily determined by one of skill in the art. For example, purified DMDD can be administered orally in an amount of between 10 mg and 1000 mg per day, as a medication, nutritional supplement, or food additive. As another example, DMDD can be administered in dosages ranging from 0.01 mg/kg to 10 mg/kg body weight, or higher; or in a form sufficient to provide a daily dosage of 0.03 mg/kg body weight to about 10 mg per/kg body weight of the subject to which it is to be administered, or alternatively for a total daily dosage of up to 1000 mg. In a diabetic mouse model, the effective dosage of DMDD was found to be approximately 12.5-25 mg/kg. A suitable dosage for human subjects can be calculated as approximately 10% of the dosage for mice, therefore an example of a calculated effective dose for a 60 kg human is 75-150 mg/person/day. Dosages and dosing regimens that are suitable for other cyclohexanediones may be suitable for therapeutic or prophylactic administration of DMDD.

DMDD can also be administered as an extract obtained from a plant source, such as a root. For example, DMDD can be administered as a powdered extract in loose, capsule or tablet form.

A physician having ordinary skill in the art can readily determine and prescribe the effective amount of the pharmaceutical composition required. For example, the physician can start doses of the DMDD employed in the pharmaceutical composition at levels lower than that required in order to achieve the desired therapeutic effect and gradually increase the dosage until the desired effect is achieved.

DMDD can be administered alone or in combination with other therapeutics via a variety of routes of administration. Administration of DMDD can occur before, during, and/or after other treatments. Such combination therapy can involve the administration of DMDD before, during and/or after the use of other anti-cancer agents, for example, chemotherapeutic agents or radiation or both. Examples of combination therapy may involve two or more therapeutic agents being administered concurrently, or being separately administered in an alternating or other periodic fashion, or being administered in succession over time. DMDD may potentiate the effects of cytokines, chemotherapeutic agents, or gamma radiation. The administration of DMDD can be separated in time from the administration of other anti-cancer agents by hours, days, or even weeks. Additionally or alternatively, the administration of DMDD can be combined with other biologically active agents or modalities such as, but not limited to, an antineoplastic agent, and non-drug therapies, such as, but not limited to, surgery.

Combination therapy is often used for the treatment of breast cancer, and can also be used prophylactically for persons at high risk of developing breast cancer. DMDD can advantageously be utilized in combination with any desired anti-cancer therapeutic agent. Illustrative chemotherapeutic agents that can be used in combination with DMDD include, without limitation, anthracyclines (such as doxorubicin/Adriamycin® and epirubicin/Ellence®); taxanes (such as paclitaxel/Taxol® and docetaxel/Taxotere®); fluorouracil (5-FU); cyclophosphamide (Cytoxan®); carboplatin; trastuzumab (Herceptin®) and Pertuzumab (Perjeta®). DMDD can be substituted for, or used in addition to, any of the commonly used drug combinations for breast cancer. Examples of commonly used combinations (in which DMDD can be substituted, or used in addition) used for early treatment of breast cancer include:

CAF (or FAC): cyclophosphamide, doxorubicin (Adriamycin), and 5-FU

TAC: docetaxel (Taxotere), doxorubicin (Adriamycin), and cyclophosphamide

AC→T: doxorubicin (Adriamycin) and cyclophosphamide followed by paclitaxel (Taxol) or docetaxel (Taxotere), or the reverse order, with the T (paclitaxel or docetaxel) given first, followed by AC, with carboplatin optionally added to paclitaxel FEC→T, 5-FU, epirubicin, and cyclophosphamide followed by docetaxel (Taxotere) or paclitaxel (Taxol), or the reverse order, with carboplatin optionally added to paclitaxel TC: docetaxel (Taxotere) and cyclophosphamide TCH: docetaxel, carboplatin, and trastuzumab (Herceptin)

CMF: cyclophosphamide (Cytoxan®), methotrexate, and 5-fluorouracil (fluorouracil, 5-FU)

A→CMF: doxorubicin (Adriamycin), followed by CMF

EC: epirubicin (Ellence) and cyclophosphamide

AC: doxorubicin (Adriamycin) and cyclophosphamide

Examples of chemotherapeutic agents useful in treating women with advanced breast cancer, which can be used in combination with DMDD, include docetaxel, paclitaxel, platinum agents (cisplatin, carboplatin), vinorelbine (Navelbine®), capecitabine (Xeloda®), liposomal doxorubicin (Doxil®), gemcitabine (Gemzar®), mitoxantrone, ixabepilone (Ixempra®), albumin-bound paclitaxel (nab-paclitaxel or Abraxane®) and eribulin (Halaven®).

Also, DMDD can be administered to a subject who has recovered from cancer, preferably breast cancer, as a maintenance medication after remission has been achieved, to help maintain remission.

Nutritional Supplement and Food Additive

DMDD can be packaged as a nutritional, health or dietary supplement (e.g., in pill or capsule form). Additionally, DMDD can be added to a food product to yield what is commonly referred to as a "nutraceutical" food or "functional" food. Foods to which DMDD can be added include, without limitation, cereals, soups and beverages.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1 Anti-cancer Activity of 2-Dodecyl-6-methoxycyclohexa-2,5-diene-1,4-dione Summary 2-Dodecyl-6-methoxycyclohexa-2,5-diene-1,4-dione (DMDD) is a cyclohexanedione found in the roots of *Averrhoa carambola L.*, commonly known as starfruit. Researchers have shown that DMDD has significant therapeutic potential for the treatment of diabetes, however the effects of DMDD on human cancers have never been reported. We investigated the effects of DMDD on human breast carcinoma cells in vitro and further examined the molecular mechanisms of DMDD-induced apoptosis in human breast carcinoma cells. DMDD suppressed the growth of breast carcinoma cells, but not normal breast cells, via induction of G0-G1 phase cell cycle arrest, oxidative stress and apoptosis. DMDD-induced cell apoptosis involved the activation of both the intrinsic mitochondrial pathway and the extrinsic receptor pathway. DMDD also increased the level of intracellular reactive oxygen species (ROS) and DMDD-induced ROS generation was found to be associated with the mitochondrial activity. In addition, DMDD inhibited LPS induced TNF-α production, as well as TNF-α activated NF-κB translocation. Collectively, our studies indicate that DMDD has significant potential as a safe and efficient therapeutic agent for the treatment of breast cancer. We demonstrated that the cyclohexanedione DMDD dramatically inhibits the proliferation of human breast carcinoma cells in vitro, but has little toxicity to normal breast cells. We further investigated the molecular mechanism of the anti-proliferation effects, and demonstrated that DMDD suppresses the growth of breast carcinoma cells via induction of G0-G1 phase cell cycle arrest, apoptosis, oxidative stress, and inhibition of TNF-α production and NF-κB activation.

Materials and Methods

Plant Materials and Extraction and Isolation of DMDD

*Averrhoa carambola L.* was collected from Linshan County, Guangxi Autonomous Region, China, in June 2010 and was identified by Prof. Lai Mao-xiang. The voucher specimen (No. 20100605) was deposited in the Guangxi Institute of Chinese Medicine & Pharmaceutical Science herbarium (Guangxi, China). The isolation of DMDD was performed as described by Zheng et al. (4).

Cell Culture

BT20 and MCF-7, human breast carcinoma cell lines (ATCC), were maintained in RPMI 1640 and Dulbecco's Modified Eagle Medium (DMEM) (Sigma), respectively. THP-1, a human monocytic leukemic cell line (ATCC), was maintained in RPMI 1640. HMEC, a normal human mammary epithelial cell line (ATCC), was maintained in McCoy's 5A (ATCC). All mediums were supplemented with 10% fetal bovine serum (FBS) (Gibco) and 1% penicillin-streptomycin and all cells were incubated in a humidified atmosphere with 5% $CO_2$ at 37° C.

Anti-Proliferation Assay and $IC_{50}$ Determination

The proliferation inhibition potential of DMDD was determined in human breast cancer cell lines MCF-7 and BT20 by a fluorescence dye staining method with the normal cell line HMEC serving as a control. Cells were seeded at a density of $4\sim5\times10^3$ cells/well in a 96-well tissue culture-treated plate (Corning Costar) and were incubated overnight. They were then treated with DMDD at final concentrations of 320 μM, 100 μM, 32 μM, 10 μM, 3.2 μM, 1 μM, and 0.32 μM. An experimental control with cells only was also included. After incubation for 48 h, the viability of cells was assessed using PrestoBlue dye (Invitrogen) according to manufacturer's protocol. The fluorescence intensity was measured on a SpectraMax M2e microplate reader (Molecular Devices, Inc.) at a fluorescent excitation wavelength of 555 nm and emission wavelength of 590 nm. The results were expressed as a percentage, relative to untreated control cells, and the half maximal inhibitory concentration ($IC_{50}$) values were calculated using non-linear regression analysis.

Multi Parameter Cytotoxicity Measurement

MCF-7 and BT20 cells were seeded in a 96-well plate (Corning Costar) at a density of 4,000 cells/well and subsequently treated with different concentrations (10, 32, 100 μM) of DMDD for 48 h. Non-treated cells and cells treated with 100 μM Valinomycin were used as negative (control) and positive controls, respectively. Afterwards, the cells were stained with a mixture of fluorescent dyes including Hoechst 33342, cell permeability dye and mitochondrial membrane potential dye (Thermo Scientific). These dyes indicated changes in nuclear morphology (Channel 1), cell membrane permeability (Channel 2) and mitochondrial transmembrane potential (Channel 3), respectively. The cells were fixed and washed, and images for each fluoroprobe were acquired at different channels using suitable filters with a 20× objective and analyzed on the Arrayscan VTI HCS Reader (Thermo Scientific). The Cell Health Profiling BioApplication (Thermo Scientific) was used for image acquisition and analysis. For each well, at least 400 cells were automatically acquired and analyzed. The average fluorescent intensity was used to quantify changes in each channel.

Apoptosis Assay

MCF-7 and BT20 cells were seeded in a 96-well plate (Corning Costar) at a density of 8,000 cells/well and were subsequently treated with different concentrations (10, 32, 100 μM) of DMDD for 48 h. Afterwards, the cells were stained with Annexin V (Millipore) and 7-Aminoactinomycin (7-AAD) (Millipore), and analyzed on a Guava flow cytometer using InCyte software (Millipore).

Cytochrome c Release Assay

MCF-7 and BT20 cells were seeded in a 96-well plate (Corning Costar) at a density of 8,000 cells/well and were subsequently treated with 100 μM of DMDD for 48 h. The percentage of cells releasing cytochrome c from mitochondria was determined using the FlowCellect Cytochrome c Kit (Millipore) according to the manufacturer's protocol. Briefly, cells were permeabilized, fixed, and stained with either anti-IgG1-FITC Isotype control or anti-Cytochrome c-FITC dye. Data was acquired and analyzed using a Guava flow cytometer and InCyte software (Millipore).

Caspase 3/7 and Caspase 8 Activation Assay

Caspase 3/7 and caspase 8 activities were analyzed using an in-situ luminescent maker in MCF-7 and BT20 cells respectively. Cells were seeded in a white 96-well plate (Greiner), treated with 100 μM DMDD for 4 h. Caspases activity was then determined using the Caspase-Glo 3/7 Assay (Promega) or the Caspase-Glo 8 Assay (Promega) according to the manufacturer's instructions. Briefly, cells were incubated with Caspase-Glo 3/7 substrate or Caspase-Glo 8 substrate and the luminescence of each sample was measured using a SpectraMax M2e Microplate Reader (Molecular Devices).

Oxidative Stress Determination

MCF-7 and BT20 cells were seeded in a 96-well tissue culture-treated plate (Corning Costar) at a density of 8,000 cells/well and were subsequently treated with different concentrations (10, 32, 100 μM) of DMDD for 48 h. Non-treated cells served as negative control, and cells treated with 1 μM Retenone served as positive control. Afterwards, the cells were stained with Hoechst 33342 (Thermo Scientific) and dihydroethidium (DHE) (Sigma), fixed and evaluated on an ArrayScan VTI HCS Reader (Thermo Scientific). The generation of ROS in cells was quantified by the oxidation of non-fluorescent DHE to fluorescent ethidium, which subsequently binds to DNA. The Nuclear Translocation BioApplication software (Thermo Scientific) was used for image acquisition and analysis. For each well, at least 400 cells were automatically acquired and analyzed. Oxidative stress activation was assessed by the DHE staining in the nucleus and measured by the average intensity of fluorescent ethidium in the identified nuclear region (MEAN_CircAvgIntenCh2).

Cell Cycle Analysis

MCF-7 and BT20 cells were first synchronized in the G0 phase by culturing cells for 24 h in serum-free medium, and then treated with 100 μM DMDD for 24 h. Cell cycle analysis was performed using propidium iodide (PI) (Millipore) staining as described (27). Cells were analyzed using a Guava flow cytometer with InCyte software (Millipore).

Human TNF-α ELISA

THP-1 cells were seeded in a 96 well plate at a density of $5 \times 10^5$ cells/well, and incubated with 100 nM phorbol-12-myristate-13-acetate (PMA) (Sigma) for 72 h. After washing the wells with warm RPMI 1640 medium, cells were pretreated with various concentrations of DMDD (10, 32, 100 μM) for 30 minutes followed by 100 ng/ml Salmonella enterica serotype typhimurium lipopolysaccharide (LPS) (Sigma). Dexamethasone at 1 μM (Sigma) was used as a positive control. After 4 h of stimulation, supernatants were collected for the quantification of human TNF-α using the Duoset enzyme-linked immunosorbent assay (ELISA) development kit (R&D Systems). AlamarBlue cell viability reagent (Invitrogen) was used to access cell integrity, after the supernatant was removed, at a fluorescent excitation wavelength of 555 nm and emission wavelength of 590 nm.

Inhibition Assay of TNF-α Activated NFκB Translocation

MCF-7 cells were seeded in a 96 well plate (Corning Costar) at a density of 8,000 cells/well and then treated with 100 μM DMDD for 2 h, followed by the addition of 10 ng/ml tumor necrosis factor-alpha (TNF-α) (Sigma). Untreated cells and cells treated with 10 ng/ml TNF-α alone served as controls. Cells were fixed, permeabilized, and sequentially stained with Nuclear factor kappa B (NF-κB) primary antibody, Dylight 488-conjugated secondary antibody, and Hoechst 33342 dye. The Hoechst and DyLight fluorophores detect changes in nuclear morphology (blue fluorescence) and NF-κB distribution (green fluorescence), respectively. The samples were analyzed on an Arrayscan VTI HCS Reader (Thermo Scientific). The Nuclear Translocation BioApplication (Thermo Scientific) was used for image acquisition and analysis. For each well, at least 400 cells were automatically acquired and analyzed. The translocation index was calculated by measuring the average intensity difference of NF-κB between the identified cytoplasmic region and nuclear region (MEAN_CircRingAvgIntenDiffCh2).

Statistical Analysis

Statistical significance was calculated using the two-tailed Student's t test. *$P \leq 0.05$; $P \leq 0.01$; *$P \leq 0.001$.

Results

DMDD Exhibits Anti Proliferation Activity in Human Breast Cancer Cells but not Normal Cells.

We evaluated the anti-proliferation activity of DMDD in the human breast carcinoma cell lines MCF-7 and BT20, and in a normal human mammary epithelial cell line HMEC as a control. We observed a concentration dependent antiproliferation effect of DMDD in MCF-7 and BT20 cells, with $IC_{50}$ values of 3.44 μM and 5.03 μM for MCF-7 and BT20 cells, respectively (FIG. 1), after 48 h treatment. In contrast to the results in cancer cells, DMDD exhibited little effect on normal HMEC cells with an $IC_{50}$ value of 48.08 μM for HMEC cells. Treatment with 10 μM DMDD caused 84.5% and 63.5% cell death in MCF-7 and BT20 cells, respectively, but only 12.7% cell death in HMEC cells. Treatment with 3.2 μM DMDD caused 49.9% and 43.8% cell death in MCF-7 and BT20 cells, respectively, but HMEC cells were not affected. These results suggest that DMDD has selective cytotoxicity for breast cancer cells.

A morphological examination of the MCF-7 and BT20 cells was performed using an inverted microscope. The MCF-7 and BT20 cells treated with DMDD for 24 and 48 h showed significant morphological changes, which are characteristic of apoptotic cells, such as cell shrinkage and reduced cell density (data not shown).

DMDD Causes Nuclear Condensation, Increase of Cell Permeability and Disruption of Mitochondrial Potential in Cancer Cells.

Figure 2:
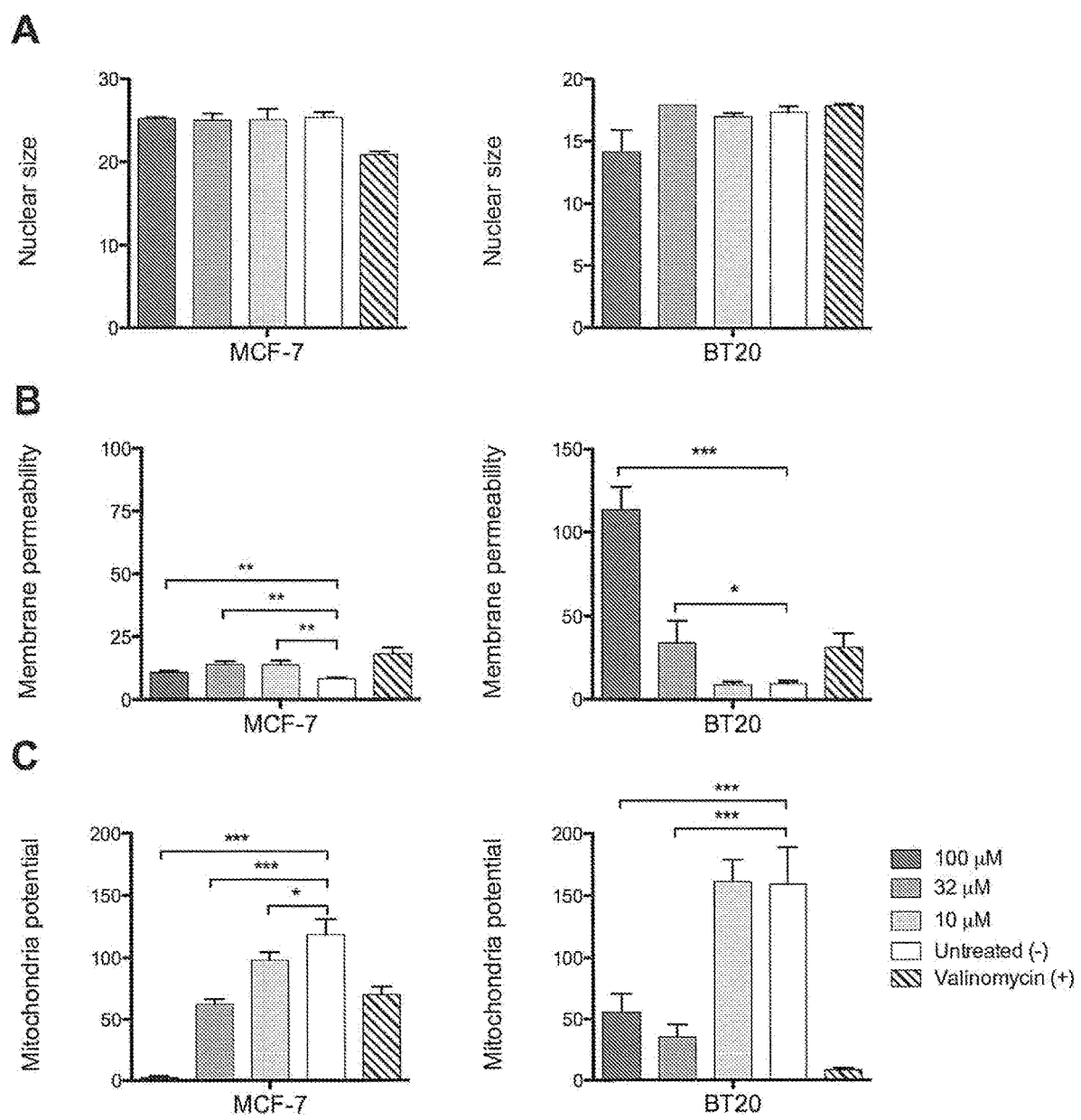
FIG. 2 shows the effect of different concentrations of DMDD on cell characteristics of MCF-7 and BT20 cells including A, nuclear size, B, membrane permeability, and C, mitochondrial membrane potential. Multiplex HCS analysis of DMDD-induced cytotoxicity in MCF-7 and BT20 cells. Cells were treated with different concentrations of DMDD for 48 h and the alteration in nuclear size, cell permeability, and mitochondrial membrane potential was simultaneously quantified by a HCS reader. Values are means±SD of three independent experiments. *$P≤0.05$; $P≤0.01$; *$P≤0.001$.

We examined the cellular changes of DMDD treated cells including nuclear morphology, cell membrane permeability and mitochondria membrane potential (ΔΨm), in parallel using high-content screening (HCS) analysis. The change of nuclear morphology was monitored by Hoechst dye staining. The cell membrane permeability was monitored by a permeability dye which stains nuclei in permeabilized cells. Mitochondrial integrity was examined by a mitochondrial membrane potential dye which accumulates in healthy mitochondria with intact membrane potential, but not in depolarized mitochondria. Untreated MCF-7 and BT20 cells displayed normal nuclear size, intact plasma membrane integrity and brightly labeled mitochondria. After 48 h treatment with DMDD, cells exhibited increased plasma membrane permeability as evidenced by higher green florescence intensity and loss of mitochondrial potential as evidenced by lower red florescence intensity, suggesting that they were undergoing severe cellular injury. In addition, the cytotoxicity effects of DMDD occurred in a dose-dependent manner as quantified in FIG. 2. The cytotoxicity effect was more dramatic in BT20 cells, as evident by the higher increase of cell membrane permeability. BT20 cells at 100 μM also exhibited nuclear condensation.

DMDD Induces Both the Intrinsic and Extrinsic Apoptosis Pathways in Human Breast Cancer Cells.

Figure 3:
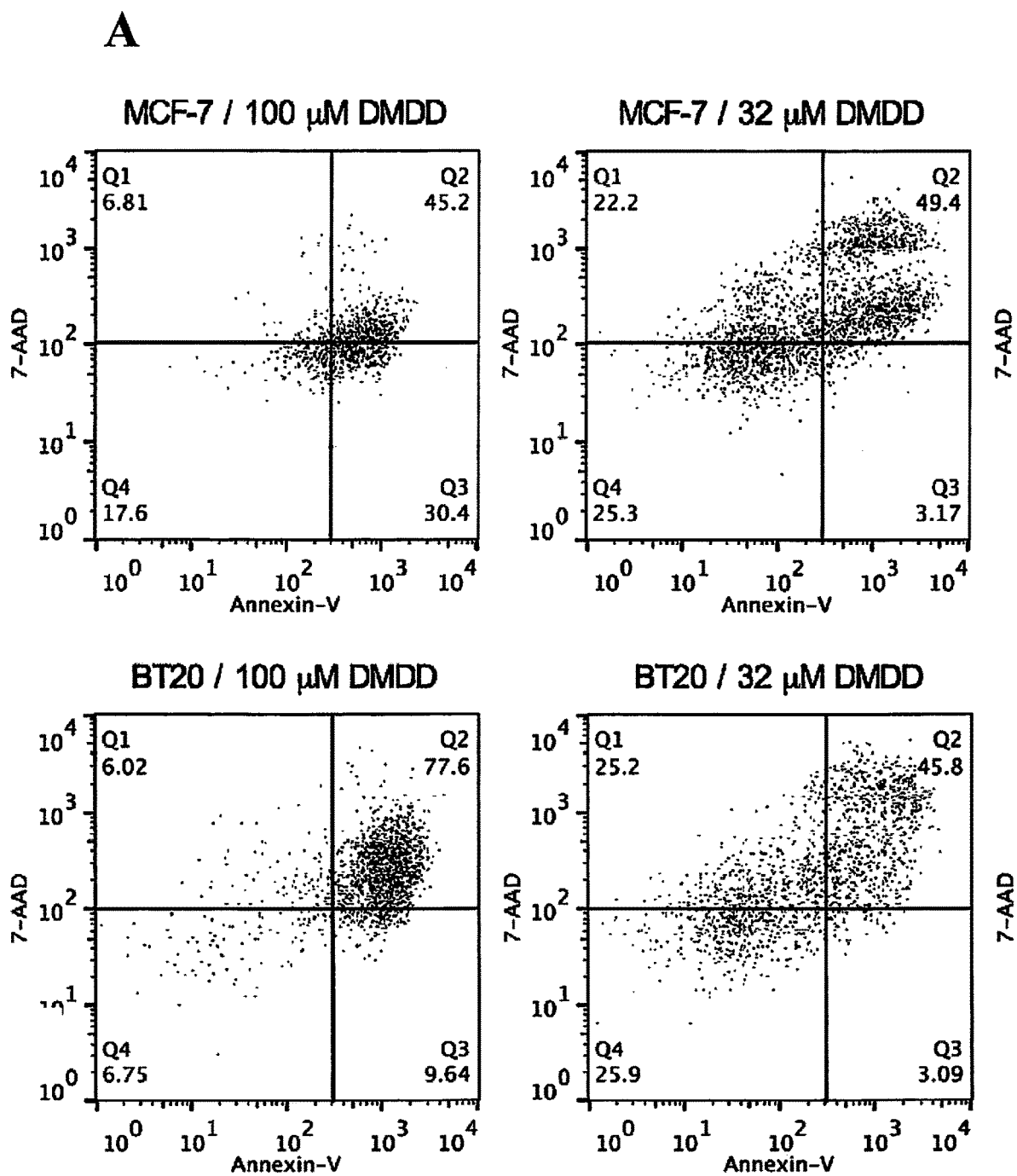
FIG. 3 shows the effect of different concentrations of DMDD on apoptosis and apoptosis-related signaling cascades in human breast carcinoma cells MCF-7 and BT20 cells. A, Flow cytometry analysis of apoptosis induced by DMDD in MCF-7 and BT20 cells. B, Percentage of apoptosis induced by different concentrations of DMDD in MCF-7 and BT20 cells. Cells were treated with different concentrations of DMDD for 48 h and assessed using Annexin V/7-AAD double staining. C, D, Caspase 3/7 and caspase 8 activation in MCF-7 and BT20 cells treated with DMDD. Cells were treated with different concentrations of DMDD for 4 h and assessed using Caspase-Glow 3/7 or Caspase-Glow 8 assay. The untreated cells served as the negative control. E, Induced cytochrome c release by DMDD. The curve on the left shows the isotype control, the curve on the right shows the negative control (untreated cells), and the middle curve shows the treated samples. Cells were treated with different concentrations of DMDD for 48 h, and the release of cytochrome c was assessed using anti-Cytochrome c-FITC staining. The error bars indicate the standard deviation from three independent experiments. *$P≤0.05$; $P≤0.01$; *$P≤0.001$.
Figure 3:
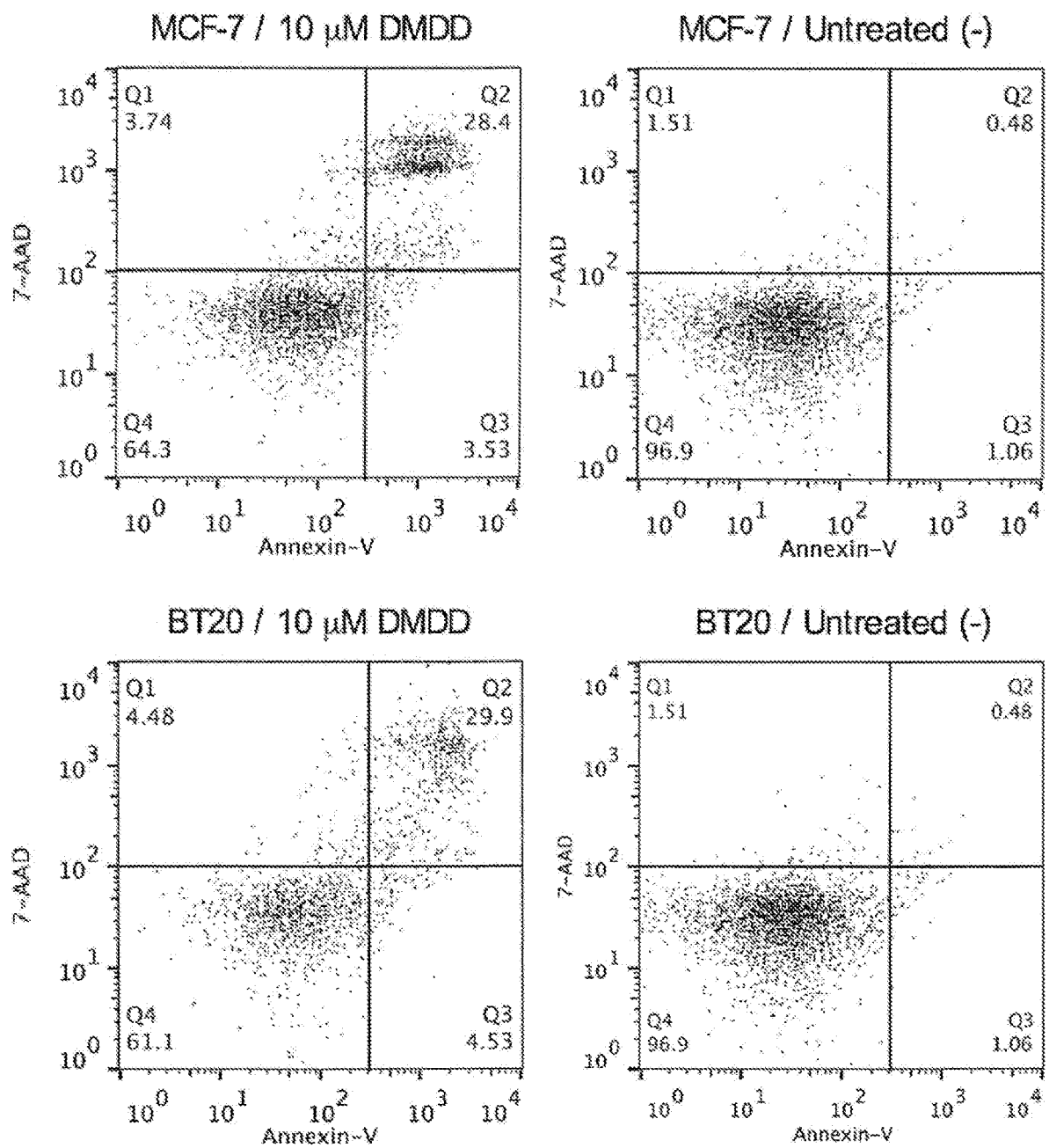
Figure 3:
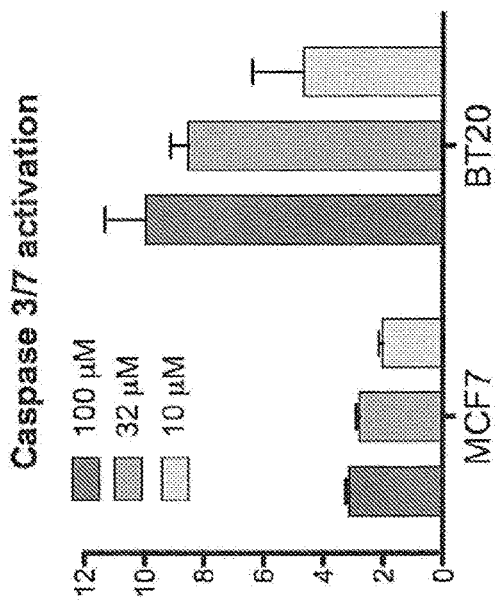
Figure 3:
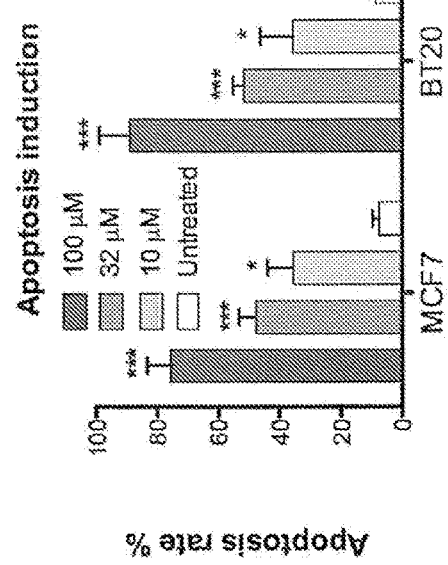
Figure 3:
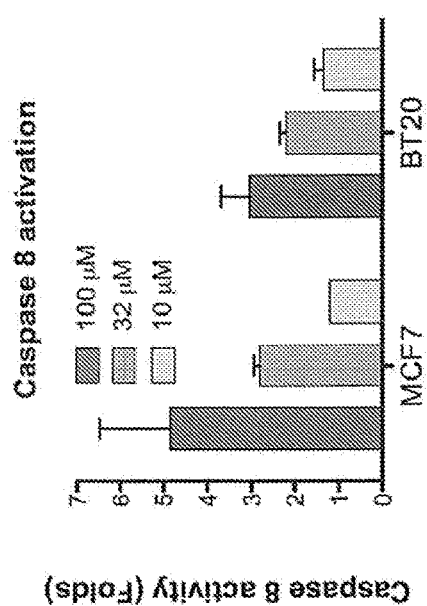
Figure 3:
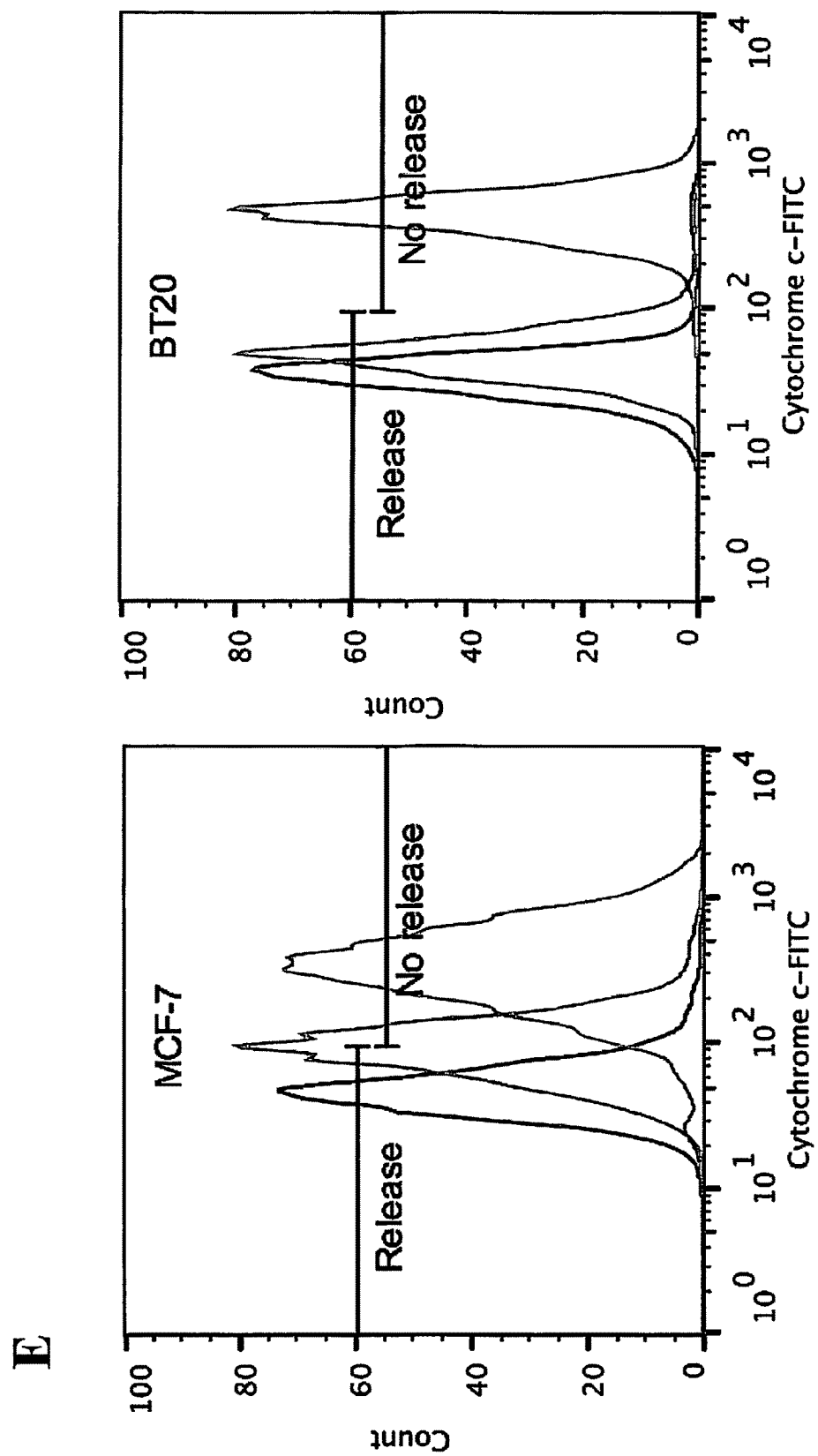

To observe the characteristic apoptotic phenotypes, we employed the Annexin V/7-AAD double staining assay to confirm that DMDD promotes apoptosis in MCF-7 and BT20 cells. We found that DMDD induced apoptosis in MCF-7 and BT20 cells (FIG. 3, panel A) and that the apoptosis induction was concentration-dependent (FIG. 3, panels A and B).

Next, we evaluated caspase 3/7 which induces apoptosis, and caspase 8, an early apoptotic marker and initiator of the extrinsic pathway in mammalian cells (28), using luminescence assays. As shown in FIG. 3, panel C, in MCF-7 and BT20 cells treated with DMDD for 4 h, the activities of caspase 3/7 increased significantly in a concentration-dependent manner compared to untreated cells. In addition, as shown in FIG. 3, panel D, in MCF-7 and BT20 cells treated with DMDD for 4 h, the activities of caspase 8 also increased about 2-5 fold depending on the concentration.

To further clarify whether DMDD also induced the intrinsic apoptosis pathway, we determined whether cytochrome c was released from the mitochondria of the treated cells. As shown in FIG. 3, panel E, cytochrome c was released from the MCF-7 and BT20 cells treated by DMDD for 48 h. Collectively our data suggests that DMDD induces apoptosis via both the extrinsic and intrinsic pathways.

DMDD Induces Oxidative Stress in Human Breast Cancer Cells.

Figure 4:
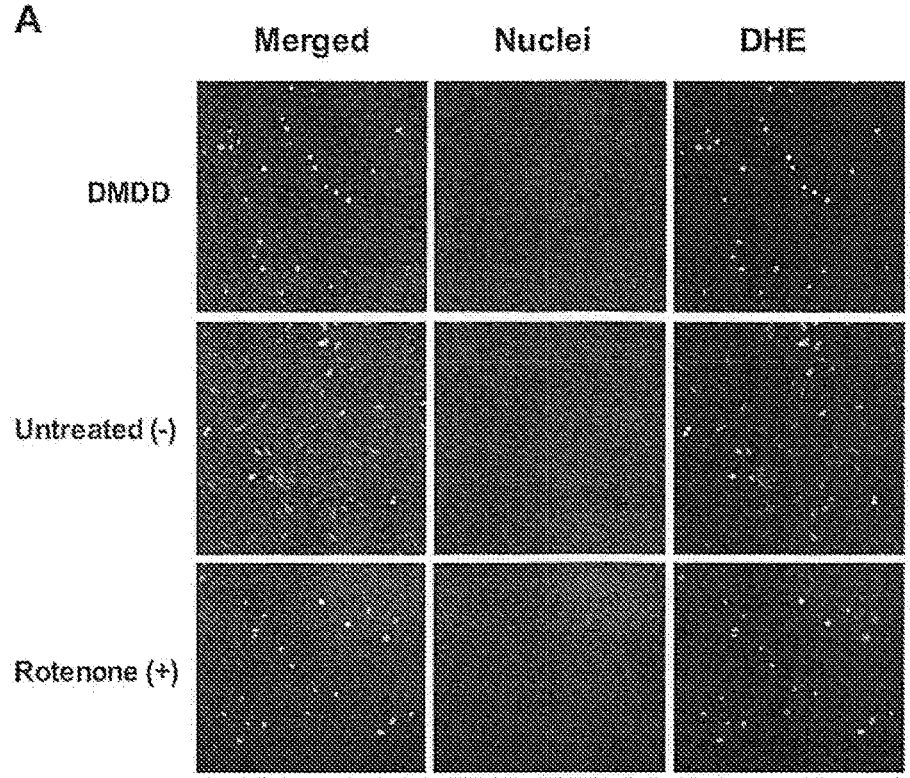
FIG. 4 shows the effect of DMDD on oxidative stress induction in human breast carcinoma cells MCF-7 and BT20. A, BT20 cells were treated with DMDD (100 μL) B, Cells were treated with different concentration of DMDD for 48 h, and the ROS level was assessed using DHE staining on a HCS reader and expressed as MEAN_CircAvgIntenCh2 as described in Materials and Methods. The error bars indicate the standard deviation from three experiments. *$P≤0.05$; $P≤0.01$; *$P≤0.001$.
Figure 4:
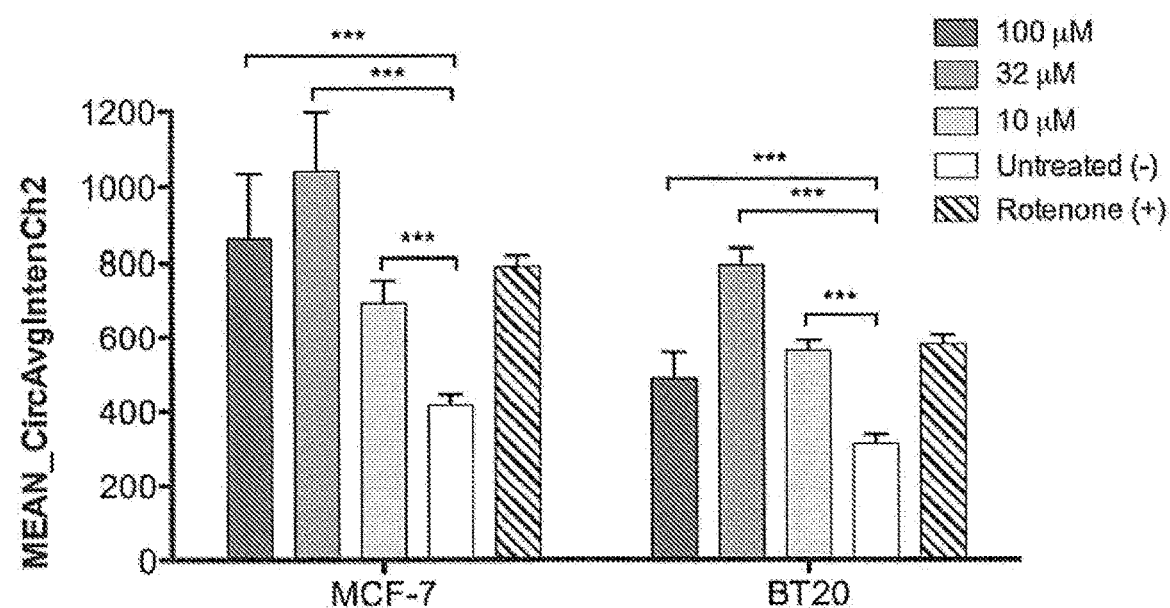

We determined the effect of DMDD on cellular ROS levels in MCF-7 and BT20 cells using HCS and an oxidative stress assay. The generation of ROS in cells was quantified by the oxidation of non-fluorescent dihydroethidium (DHE) to fluorescent ethidium. As showed in FIG. 4, 48-h treatment with DMDD caused a marked increase in ROS generation in both MCF-7 and BT-20 cells. An intermediate concentration of DMDD (33 μM) enhanced ROS levels nearly three-fold versus the non-treated control, while high and low concentrations (100 μM and 10 μM) of DMDD enhanced ROS nearly two-fold versus the untreated control.

DMDD Arrests the Cell Cycle of Cancer Cells at G1 Phase.

Figure 5:
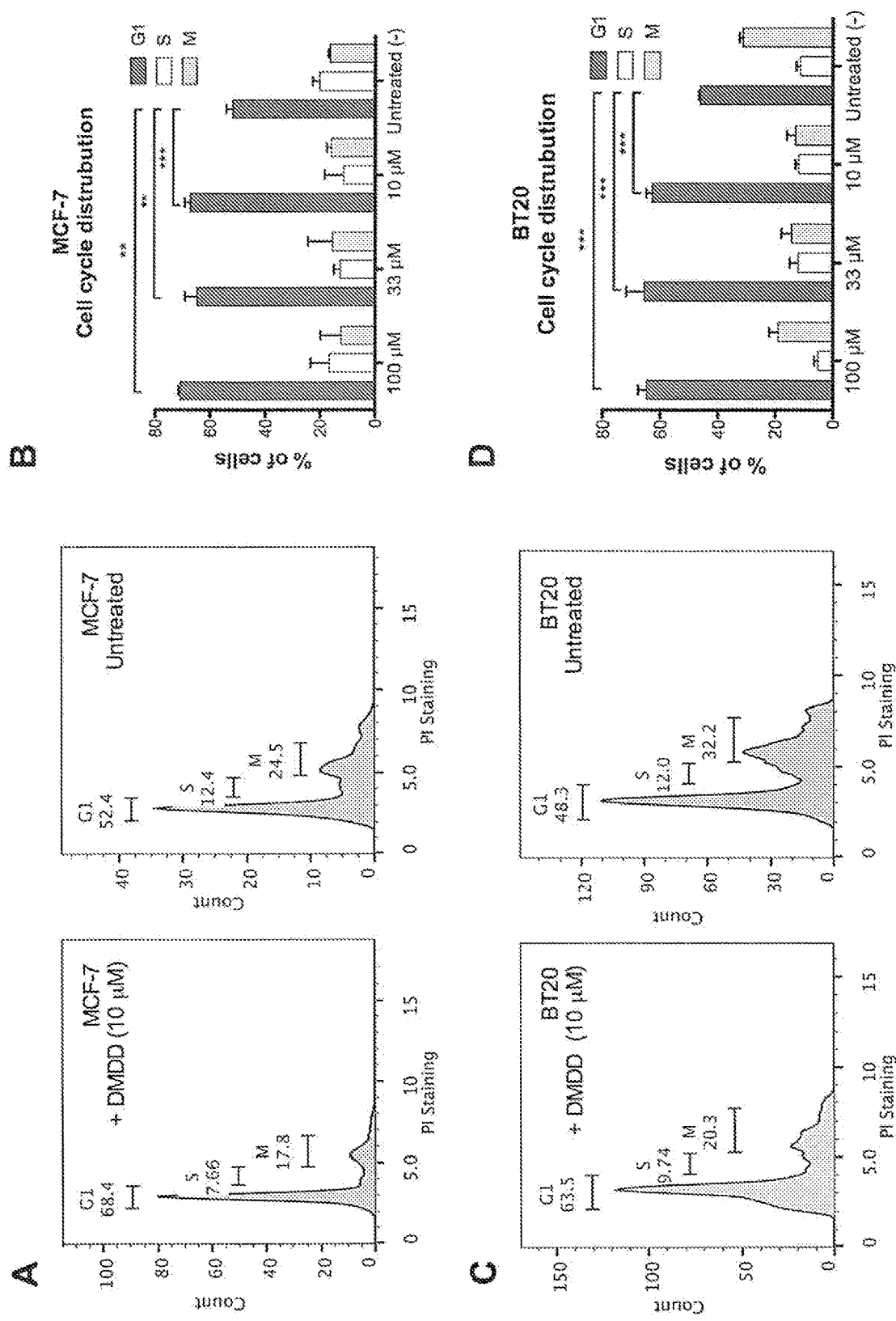
FIG. 5 shows the cell cycle distribution of human breast carcinoma cells MCF-7 and BT20 treated with DMDD. Cells were synchronized for 24 h prior to the treatment with different concentrations of DMDD for 24 h and assessed using propidium iodide (PI) staining. A, C, The cell cycle distribution of MCF-7 cells treated with DMDD. B, D, The cell cycle distribution of BT20 cells treated with DMDD. The error bars indicate the standard deviation from three experiments. *$P≤0.05$; $P≤0.01$; *$P≤0.001$.

To examine if DMDD altered the distribution of the cell cycle, we performed a cell cycle analysis with MCF-7 and BT-20 cells. As shown in FIG. 5, DMDD induced a significant increase in the cell number at the G1 phase, with a corresponding decrease in the S and G2-M phases in both breast cancer cell lines. In MCF-7 cells, the percentage of G1 phase cells increased from 52% to 71%; and in BT20 cells, the percentage of G1 phase cells increased from 46% to 65%. These results suggest that DMDD disrupts the G1-S transition during cell division. The alteration of the cell cycle was not concentration-dependent.

DMDD Inhibits TNF-α Production in LPS Induced THP-1 Cells.

Figure 6:
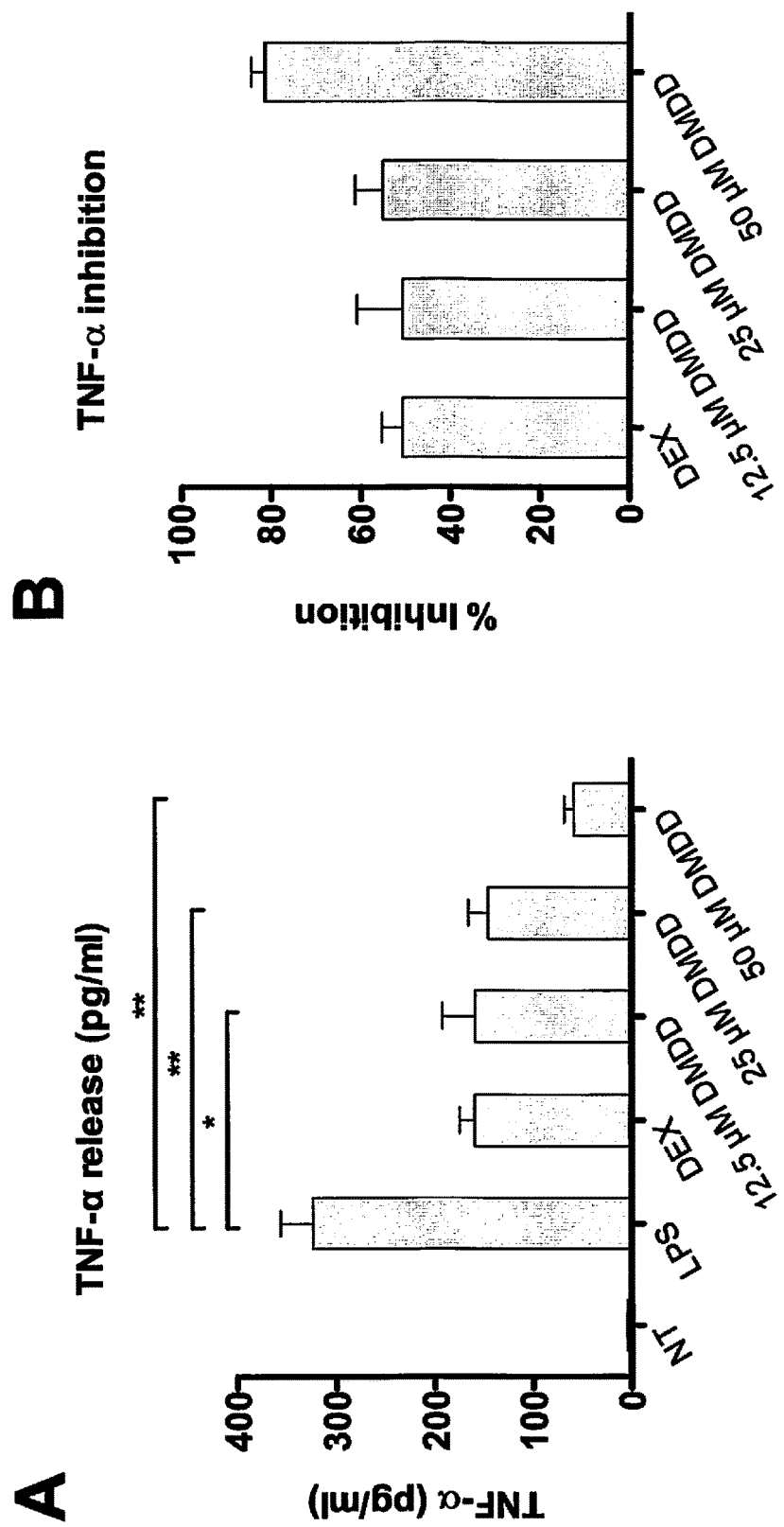
FIG. 6 shows the inhibition caused by DMDD on LPS-induced TNF-α production in the THP-1 cell line. A, $5×10^5$ cells/ml of PMA (100 nM)-treated THP-1 cells were pretreated for 30 min with 1 μM dexamethasone and various concentrations of DMDD followed by 100 ng/ml LPS stimulation for 4 h. Supernatants were collected and the TNF-α level was measured using a hu-TNF-α ELISA. B, Relative percent inhibition of TNF-α by DMDD. Following treatments the medium was replaced with 1× Alamarblue reagent in RPMI 1640 medium and incubated for 20-24 h at 37° C. and 5% $CO_2$. Fluorescence was measured at excitation 555 nm and emission 590 nm and relative percent viability against the no treatment control was determined. The error bars indicate the standard deviation from three independent experiments. *$P≤0.05$; $P≤0.01$; *$P≤0.001$.

To determine whether DMDD affected cytokine production in LPS-induced THP-1 cells, human TNF-α ELISA was used to assess the level of tumor-necrosis factor-alpha (TNF-α) in the supernatant. THP-1 cells were pretreated with 12.5-50 μM of DMDD for 30 min followed by stimulation with 100 ng/ml LPS for 4 h. 1 μM of dexamethasone was used as a positive control for TNF-α inhibition. Cell integrity after the treatments was measured using AlamarBlue reagent to determine the viability of the cells. DMDD did not affect the viability of THP-1 cells after the treatment with or without LPS stimulation (data not shown). As FIG. 6 shows, DMDD caused a significant reduction of the TNF-α level in the supernatants of the cell cultures relative to the cells treated with LPS alone (FIG. 6, panels A and B).

DMDD Inhibits TNF-α Activated NF-κB Translocation.

Figure 7:
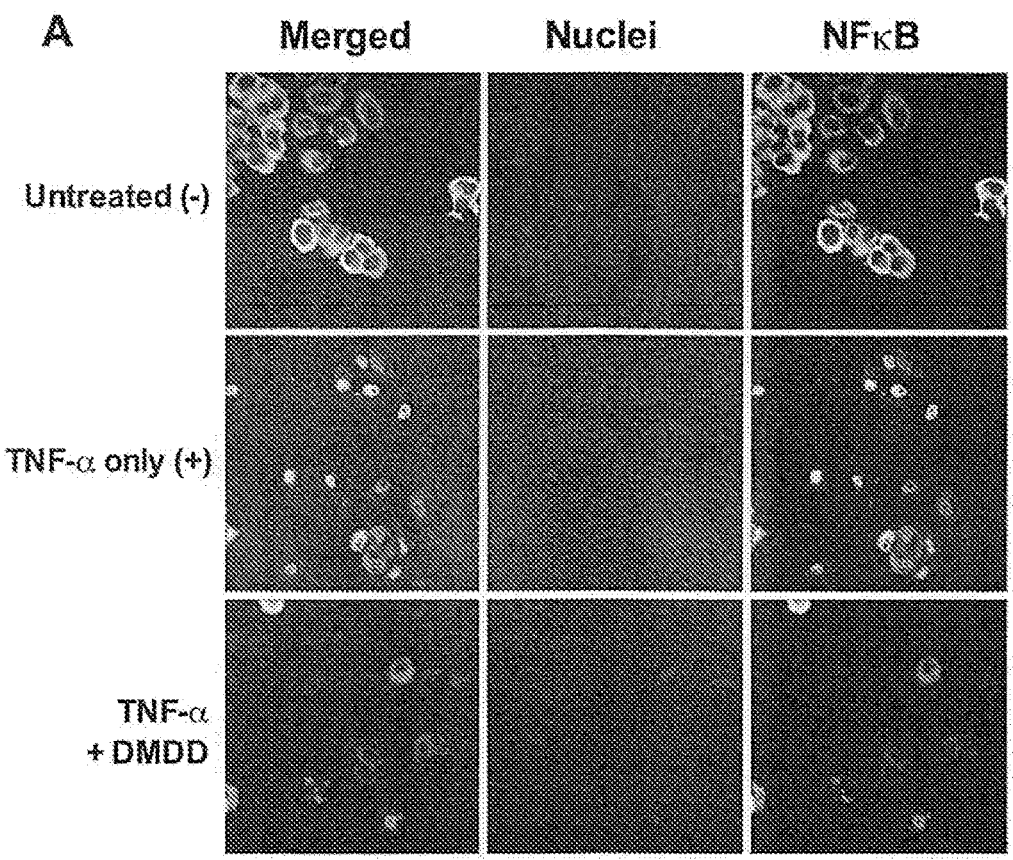
FIG. 7 shows the inhibition caused by DMDD on TNF-α activated NF-κB nuclear translocation in human breast carcinoma cells MCF-7 and BT20. A, HCS images of the NF-κB translocation. B, Values of NF-κB nuclear translocation in MCF-7 cells after the treatment with different concentrations of DMDD. Cells were treated with different concentration of DMDD for 2 h, followed by stimulation with 10 ng/ml TNF-α. Cells treated with TNF-α alone served as the negative control. The translocation index was expressed as MEAN_CircRingAvgIntenDiffCh2 as described in Materials and Methods. The error bars indicate the standard deviation from three independent experiments. *$P≤0.05$; $P≤0.01$; *$P≤0.001$.
Figure 7:
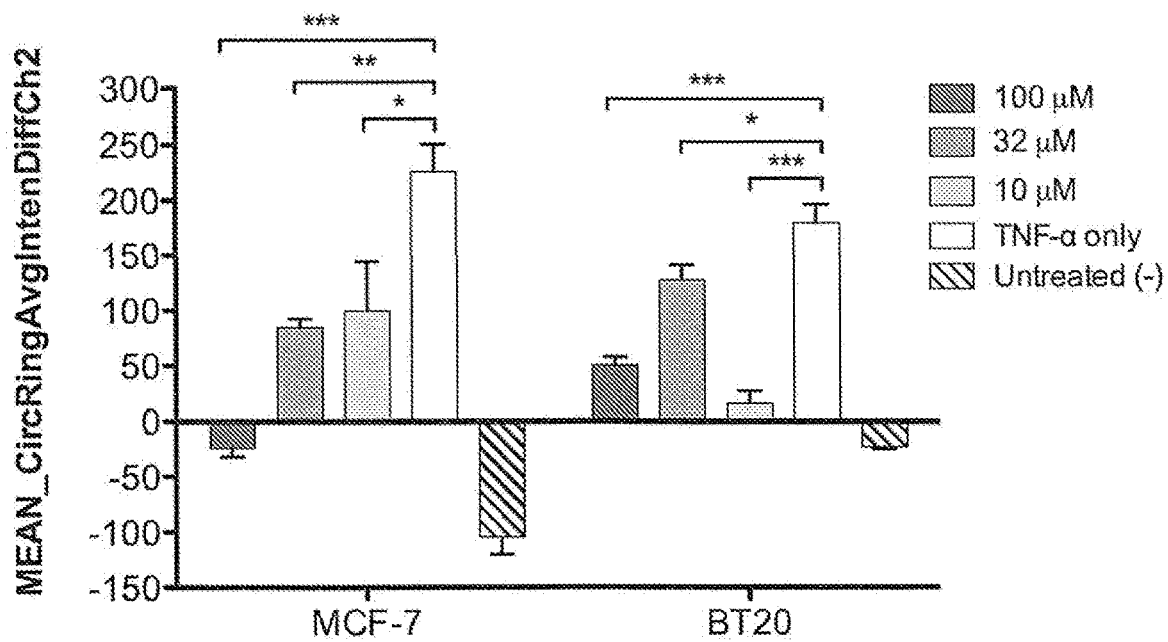

We assessed the ability of DMDD to inhibit NF-κB activation induced by the inflammatory cytokine TNF-α by using anti-NF-κB antibody conjugated fluorescent dye to monitor the NF-κB translocation from the cytoplasm to nuclear region. As shown in FIG. 7, panel A, in non-treated MCF-7 cells, a high fluorescence intensity of NF-κB was found in the cytoplasm, but rarely in the nuclei, indicating that NF-κB is not activated under normal conditions. Following stimulation with TNF-α, the NF-κB fluorescent intensity significantly increased in the nuclear region, indicating NF-κB translocation from the cytoplasm to the nucleus. We observed significant inhibition of TNF-α-induced NF-κB nuclear translocation in both MCF-7 and BT20 cells treated with DMDD as evidenced by decreased intranuclear NF-κB fluorescence intensity (FIG. 7, panel B). In MCF-7 cells, concentration-dependent inhibition was observed; however, in BT20 cells, the lowest concentration (10 μM) yielded more significant inhibition than medium (32 μM) and high (100 μM) concentrations.

Discussion

Previous studies have shown that cyclohexanedione and their derivatives possess anticancer activities (8). In this study, we demonstrated that the cyclohexanedione DMDD has dramatic and selective cytotoxicity towards human breast cancer cells. DMDD inhibits the growth of human breast carcinoma cell lines MCF-7 and BT20, while causing little or no toxicity to the normal breast epithelial cell line HMEC or the differentiated human monocytic cell line THP-1. In their studies on the antidiabetic effects of DMDD Zheng et al. (4) also showed that administration of a single dose of DMDD at 5,000 mg/kg body weight did not cause any acute toxicity.

The cytotoxic effect of DMDD on cancer cells was found to be accompanied by the induction of apoptosis, as evidenced by nuclear morphology and cell permeability changes using high-content screening (HCS) multiplex cytotoxicity analysis. The dose-dependent apoptosis induction was further confirmed by Annexin V/7-AAD double staining. Xu et al. (29) demonstrated that DMDD treatment significantly reduced caspase-3, -8, -9 expression and inhibited cell apoptosis in the pancreas tissue of mice. Collectively, these and our results suggest that DMDD-induced apoptosis is selective and specific to cancer cells. Caspase-8 is an initiator caspase in the extrinsic pathway of apoptosis, and in this study we showed that caspase 8 was activated in DMDD-treated MCF-7 and BT20 cells, suggesting that DMDD induces apoptosis through the extrinsic pathway.

The release of cytochrome c from mitochondria into the cytoplasm is the hallmark of the intrinsic pathway of apoptosis (30, 31). Using HCS analysis we showed that DMDD disrupted the mitochondria potential in a concentration dependent manner, and we further confirmed that the DMDD-induced apoptosis was accompanied by cytochrome c release using flow cytometry, suggesting that DMDD also induced the intrinsic pathway of apoptosis.

Many studies have demonstrated evidence of cross talk between extrinsic and intrinsic pathways in apoptosis (32, 33). In the extrinsic pathway, once caspase-8 is activated, it can either directly cleave caspase-3 or cleave BH3-only protein BH3-interacting domain death agonist (Bid), which subsequently translocates to the mitochondrial membrane, disrupts the mitochondrial transmembrane potential and releases cytochrome c (34). Therefore, it's not surprising to see that DMDD activated both signaling pathways in the breast cancer cells. In addition, we also demonstrated that the executioner caspases 3/7 were activated in DMDD-treated MCF-7 and BT20 cells.

Evidence has shown that ROS are common mediators of apoptosis, and excess ROS in the cells induce apoptosis (21). In the apoptotic process, initial stress-induced damage does not kill cells directly, rather it triggers an apoptotic signaling program that leads to cell death (35). In our study, DMDD induced significant ROS accumulation in the MCF-7 and BT20 cancer cells at 10, 33 and 100 µM. It is likely that excess generation of ROS plays a role in DMDD-induced apoptosis in these breast carcinoma cells. It is commonly known that mitochondria are one of the main sources of ROS in mammalian cells, and the generation of ROS has been suggested to be a representative pathway of mitochondrial disruption (36, 37). In this study, we found that ROS generation is also associated with mitochondrial disruption. In addition, oxidative stress causes oxidation of membrane lipids (lipid peroxidation) and lipid peroxides can prolong the G1 phase. Oxidative stress also inhibits the transition of cells from G1 to the S phase by inhibition of DNA synthesis (21). In MCF7 and BT20 breast cancer cells, DMDD was found to inhibit cell cycle progression by prolonging G1 phase and inhibiting the cell cycle transition from G1 to the S phase.

NF-κB has been associated with cancer due to its ability to create a positive feedback loop of inflammation. While NF-kB is dormant in the cytosol of normal cells, many cancer cells have been shown to possess constitutively active NF-κB, either due to mutations in the NF-κB inhibitor IκB, or in NF-kB itself that allow for its continuous activation (38). Without regulation, this ongoing activation enhances cancer cell proliferation. Unfortunately, therapeutics that specifically inhibit NF-κB also inhibit activation of the immune system reducing their efficacy in treatment regimens (39). However, we have shown that DMDD induces apoptosis while reducing activation of NF-κB and its translocation, suggesting a potential important mechanism of action for cancer therapies.

Inhibition of NF-κB activation blocks cancer cell proliferation and therefore targeting the NF-κB signaling pathway has become an important therapeutic option for cancer treatments. NF-κB may be activated from its inactive precursors by two signaling pathways: the canonical pathway (or classical pathway), which is activated in the presence of inflammatory cytokines or compounds, and the noncanonical pathway (or alternative pathway) which is activated during B cell development (23). The canonical pathway, which is most usually associated with cancer, is mainly activated by TNF-α, IL-1, and LPS (39). Our results showed that DMDD significantly reduced the TNF-α level in the cells treated with LPS, as well as dramatically inhibiting NF-κB translocation from the cytoplasm to the nuclei. These results suggest that DMDD serves as an inhibitor to the canonical NF-κB pathway in human breast carcinoma cells, playing a role in preventing the initial inflammatory cascade in cancer cells that drives further proliferation. Although mild ROS levels can lead to modest NF-κB activation, excessive ROS level can inhibit NF-κB activation (17). Whereas most NF-κB inhibition seems to result from inhibition of proteolysis (41), it is possible the NF-κB inhibition could be mediated by ROS induced by DMDD.

Interestingly, a recognition of an association between breast cancer and diabetes has been emerging. A recent study followed a total of 24,976 women with breast cancer and 124,880 women without breast cancer, and observed an increase in the incidence of diabetes among breast cancer survivors (9). Previous studies have shown that women with diabetes had a 23% higher risk of breast cancer (10, 11) and up to a 50% increase in mortality following a diagnosis of breast cancer (12). This association suggests that breast cancer and diabetes may share common pathways in their progression, and that the anti-diabetic agents targeting those common pathways will potentially be beneficial to cancer treatment as well. For instance, growth hormone (GH), insulin-like growth factor-1 (IGF-1) and the mammalian target of the rapamycin (mTOR) signaling pathway has revealed a crucial involvement in the onset and progression of diabetes and cancer (42). mTOR interacts with many proteins to form at least two distinct complexes: mTOR complex 1 (mTORC1) and mTOR complex 2 (mTORC2) (43). mTORC1 plays an essential role in tumorigenesis mainly by relieving the eIF4E-binding protein 1 (4E-BP1)-mediated inhibition of eukaryotic translation initiation factor 4E (eIF4E) and driving the translation of oncogenes, whereas mTORC2 activates Akt and other AGC family proteins which promote proliferation and survival (42, 44). Collectively, mTORC1 and mTORC2 regulate many processes involved in the promotion of cell growth and proliferation, including protein synthesis, autophagy, and metabolism (45). Metformin, the anti-diabetic drug, has been shown to significantly lower the risk of cancer as compared to patients treated with other anti-diabetic drugs in recent epidemiological studies (13, 14). Many studies show that the mechanism of action of metformin is through the regulation of the AMP activated protein kinase (AMPK)/mTOR pathway (46, 47) As Zheng et al. showed, DMDD also has a significant hypoglycemic effect in vitro and in vivo (4), and taken together with the anticancer activity demonstrated in this study, raises the possibility that DMDD could exhibit efficacies similar to metformin. The ability of DMDD to inhibit the growth of human breast carcinoma cells without general toxicity indicates that DMDD is a promising candidate for cancer treatment. In addition, DMDD is of particular interest due to its potential benefits of reducing the risk of both cancer and diabetes.

REFERENCES

1. American Cancer Society. Cancer Facts & Figures 2014. Atlanta: American Cancer Society; 2014.
2. Huang, G H, Huang, C Z, Huang, R B. Effects of *Averrhoa Carambola L.* Root Polysaccharide on Serum Insulin and Index of Thymus, Spleen in STZ-induced Diabetic Mice. *Chin. Pharm.* 2009, 12, 848-850.
3. Huang, G H and Huang R B. Effects of Alcoholic Extracts of *Averrhoa carambola L.* Root on Blood Glucose Level and Lipid Peroxidation in Diabetic Mice. *Lishizhen Med. Mater. Med. Res.* 2009, 20, 2730-2731.
4. Zheng, N., Lin, X., Wen, Q., Zhang, S., Huang, J., Xu, X., & Huang, R. (2013). Effect of 2-dodecyl-6-methoxycyclohexa-2, 5-diene-1, 4-dione, isolated from *Averrhoa carambola L.* (Oxalidaceae) roots, on advanced glycation end-product-mediated renal injury in type 2 diabetic KKAy mice. *Toxicology letters,* 219(1), 77-84.
5. George, M., Jolocam, M., Odongkara, B., Twinomuhwezi, H., & Mpango, G. B. (2011). New biologically active compounds from 1, 3-diketones. *Synthesis,* 1, 3.
6. Sharma, P., Rane, N., & Gurram, V. K. (2004). Synthesis and QSAR studies of pyrimido [4, 5-d] pyrimidine-2, 5-dione derivatives as potential antimicrobial agents. *Bioorganic & medicinal chemistry letters,* 14(16), 4185-4190.
7. Dominguez, J. N., López, S., Charris, J., Iarruso, L., Lobo, G., Semenov, A., . . . & Rosenthal, P. J. (1997). Synthesis and antimalarial effects of phenothiazine inhibitors of a Plasmodium falciparum cysteine protease. *Journal of medicinal chemistry,* 40(17), 2726-2732.
8. Acton, N., Brossi, A., Newton, D. L., & Sporn, M. B. (1980). Potential prophylactic antitumor activity of retinylidene 1, 3-diketones. *Journal of medicinal chemistry,* 23(7), 805-809.
9. Lipscombe, L. L., Chan, W. W., Yun, L., Austin, P. C., Anderson, G. M., & Rochon, P. A. (2013). Incidence of diabetes among postmenopausal breast cancer survivors. *Diabetologia,* 56(3), 476-483.
10. Lipscombe L L, Goodwin P J, Zinman B, McLaughlin J R, Hux J E (2006) Diabetes mellitus and breast cancer: a retrospective population-based cohort study. *Breast Canc Res Treat* 98:349-35
11. Liao, S., Li, J., Wei, W., Wang, L., Zhang, Y., Li, J., . . . & Sun, S. (2011). Association between diabetes mellitus and breast cancer risk: a meta-analysis of the literature. *Asian Pac J Cancer Prev,* 12(4), 1061-1065.
12. Peairs K S, Barone B B, Snyder C F et al (2011) Diabetes mellitus and breast cancer outcomes: a systematic review and metaanalysis. *J Clin Oncol* 29:40-46
13. Gallagher, E. J., & LeRoith, D. (2011). Diabetes, cancer, and metformin: connections of metabolism and cell proliferation. Annals of the New York Academy of Sciences, 1243(1), 54-68.
14. Arshad, O. A., Venkatasubramami, P. S., Datta, A., & Venkatraj, J. (2013, November). Department of Electrical and Computer Engineering, Texas A&M University, College Station, USA. In Genomic Signal Processing and Statistics (ENSIPS), 2013 IEEE International Workshop on (pp. 44-44). IEEE.
15. Susin S A, Daugas E, Ravagnan L et al (2000) Two distinct pathways leading to nuclear apoptosis. *J Exp Med* 192:571-580
16. Li-Weber, M. Targeting apoptosis pathways in cancer by Chinese medicine. *Cancer Lett* 2010; 332(2): 304-312.
17. Reuter, S., Gupta, S. C., Chaturvedi, M. M., & Aggarwal, B. B. (2010). Oxidative stress, inflammation, and cancer: how are they linked? *Free Radical Biology and Medicine,* 49(11), 1603-1616.
18. Veskoukis, A. S., Tsatsakis, A. M., & Kouretas, D. (2012). Dietary oxidative stress and antioxidant defense with an emphasis on plant extract administration. *Cell Stress and Chaperones,* 17(1), 11-21.
19. Mariani, E., Polidori, M. C., Cherubini, A., & Mecocci, P. (2005). Oxidative stress in brain aging, neurodegenerative and vascular diseases: an overview. *Journal of Chromatography B,* 827(1), 65-75.
20. Galli, F., Piroddi, M., Annetti, C., Aisa, C., Floridi, E., & Floridi, A. (2005). Oxidative stress and reactive oxygen species.
21. Ozben, T. (2007). Oxidative stress and apoptosis: impact on cancer therapy. *Journal of pharmaceutical sciences,* 96(9), 2181-2196.
22. Sosa, V., Moliné, T., Somoza, R., Paciucci, R., Kondoh, H., & LLeonart, M. E. (2013). Oxidative stress and cancer: an overview. *Ageing research reviews,* 12(1), 376-390.
23. Miller, S. C., Huang, R., Sakamuru, S., Shukla, S. J., Attene-Ramos, M. S., Shinn, P., . . . & Xia, M. (2010). Identification of known drugs that act as inhibitors of NF-κB signaling and their mechanism of action. *Biochemical pharmacology,* 79(9), 1272-1280.
24. Sethi G, Tergaonkar V. Potential pharmacological control of the NFkappaB pathway. *Trends Pharmacol Sci* 2009; 30:313-321.
25. Yamamoto, Y., & Gaynor, R. B. (2001). Therapeutic potential of inhibition of the NF-κB pathway in the treatment of inflammation and cancer. *Journal of Clinical Investigation,* 107(2), 135-142.
26. Gilmore, T. D., & Garbati, M. R. (2011). Inhibition of NF-κB signaling as a strategy in disease therapy. In NF-kB in Health and Disease (pp. 245-263). Springer Berlin Heidelberg.
27. Maussang, D., Verzijl, D., van Walsum, M., Leurs, R., Holl, J., Pleskoff, O., . . . & Smit, M. J. (2006). Human cytomegalovirus-encoded chemokine receptor US28 promotes tumorigenesis. *Proceedings of the National Academy of Sciences,* 103(35), 13068-13073.
28. Boatright, K. M., & Salvesen, G. S. (2003). Mechanisms of caspase activation. *Current opinion in cell biology,* 15(6), 725-731.
29. Xu X, Liang T, Wen Q, Lin X, Tang J, Zuo Q, Tao L, Xuan F, Huang R. (2014). Protective effects of total extracts of *Averrhoa carambola L.* (Oxalidaceae) roots on Strptozotocin-induced diabetic mice. *Cellular Physiology and Biochemistry,* 33: 1272-1282
30. Tait, S. W., & Green, D. R. (2010). Mitochondria and cell death: outer membrane permeabilization and beyond. *Nature Reviews Molecular Cell Biology,* 11(9), 621-632.
31. Kluck, R. M., Bossy-Wetzel, E., Green, D. R., & Newmeyer, D. D. (1997). The release of cytochrome c from mitochondria: a primary site for Bcl-2 regulation of apoptosis. *Science,* 275(5303), 1132-1136.
32. Roy, S., & Nicholson, D. W. (2000). Cross-talk in cell death signaling. *The Journal of experimental medicine,* 192(8), F21-F26.
33. Basu, A., Castle, V. P., Bouziane, M., Bhalla, K., & Haldar, S. (2006). Crosstalk between extrinsic and intrinsic cell death pathways in pancreatic cancer: synergistic action of estrogen metabolite and ligands of death receptor family. *Cancer research,* 66(8), 4309-4318.
34. Liu, Y., Borchert, G. L., Surazynski, A., Hu, C. A., & Phang, J. M. (2006). Proline oxidase activates both intrinsic and extrinsic pathways for apoptosis: the role of ROS/superoxides, NFAT and MEK/ERK signaling. *Oncogene,* 25(41), 5640-5647.
35. Cain, K., Bratton, S. B., Langlais, C., Walker, G., Brown, D. G., Sun, X. M., & Cohen, G. M. (2000). Apaf-1 oligomerizes into biologically active ~700-kDa and inactive ~1.4-MDa apoptosome complexes. *Journal of Biological Chemistry,* 275(9), 6067-6070.
36. Matés, J. M., & Sanchez-Jiménez, F. M. (2000). Role of reactive oxygen species in apoptosis: implications for cancer therapy. *The international journal of biochemistry & cell biology,* 32(2), 157-170.
37. Ye, J., Wang, S., Leonard, S. S., Sun, Y., Butterworth, L., Antonini, J., Ding, M., Rojanasakul, Y., Vallyathan, V., Castranova, V., and Shi, X. Role of reactive oxygen species and p53 in chromium (VI)-induced apoptosis. *J. Biol. Chem.,* 274: 34974-34980, 1999.
38. Zorov, D. B., Juhaszova, M., & Sollott, S. J. (2006). Mitochondrial ROS-induced ROS release: an update and review. *Biochimica et Biophysica Acta (BBA)-Bioenergetics,* 1757(5), 509-517.
39. Voboril, R. & Weberova-Voborilova, J. Constitutive NF-kappaB activity in colorectal cancer cells: impact on radiation-induced NF-kappaB activity, radiosensitivity, and apoptosis. *Neoplasma* 53, 518-523 (2006).
40. Hoesel, B. & Schmid, J. A. The complexity of NF-κB signaling in inflammation and cancer. *Mol. Cancer* 12, 86 (2013).
41. Adams, J. Proteasome inhibition in cancer: Development of PS-341. *Semin. Oncol.* 28, 613-619 (2001).
42. Zoncu, R., Efeyan, A., & Sabatini, D. M. (2011). mTOR: from growth signal integration to cancer, diabetes and ageing. *Nature reviews Molecular cell biology,* 12(1), 21-35.
43. Laplante, M., & Sabatini, D. M. (2012). mTOR signaling. *Cold Spring Harbor perspectives in biology,* 4(2), a011593.
44. Dazert, E., & Hall, M. N. (2011). mTOR signaling in disease. *Current opinion in cell biology,* 23(6), 744-755.
45. Hsu, P. P., Kang, S. A., Rameseder, J., Zhang, Y., Ottina, K. A., Lim, D., . . . & Sabatini, D. M. (2011). The mTOR-regulated phosphoproteome reveals a mechanism of mTORC1-mediated inhibition of growth factor signaling. *Science,* 332(6035), 1317-1322.
46. Gallagher, E. J., & LeRoith, D. (2011). Diabetes, cancer, and metformin: connections of metabolism and cell proliferation. Annals of the New York Academy of Sciences, 1243(1), 54-68.
47. Arshad, O. A., Venkatasubramami, P. S., Datta, A., & Venkatraj, J. (2013, November). Department of Electrical and Computer Engineering, Texas A&M University, College Station, USA. In Genomic Signal Processing and Statistics (ENSIPS), 2013 IEEE International Workshop on (pp. 44-44). IEEE.
48. Sahra, I. B., Regazzetti, C., Robert, G., Laurent, K., Le Marchand-Brustel, Y., Auberger, P., . . . & Bost, F. (2011). Metformin, independent of AMPK, induces mTOR inhibition and cell-cycle arrest through REDD1. *Cancer research,* 71(13), 4366-4372.
49. Dowling, R. J., Zakikhani, M., Fantus, I. G., Pollak, M., & Sonenberg, N. (2007). Metformin inhibits mammalian target of rapamycin-dependent translation initiation in breast cancer cells. *Cancer research,* 67(22), 10804-10812.

What is claimed is:
1. A method for treating breast cancer in a subject, the method comprising:
   administering to the subject a composition comprising an effective amount of 2-dodecyl-6-methoxycyclohexa-2,5-diene-1,4-dione (DMDD).
2. The method of claim 1, wherein the breast cancer comprises a solid tumor disposed in the breast of the subject.
3. The method of claim 1, wherein the subject suffers from diabetes, prediabetes, or metabolic syndrome.
4. The method of claim 1, wherein the composition comprises an extract prepared from the roots of *Averrhoa carambola* L.
5. The method of claim 1, wherein the composition further comprises a pharmaceutically acceptable carrier.
6. The method of claim 1, wherein the composition further comprises at least one second therapeutic agent.
7. The method of claim 6, wherein the second therapeutic agent comprises at least one of a cytokine, a chemokine, a therapeutic antibody, an adjuvant, an antioxidant, or a chemotherapeutic agent.
8. The method of claim 6, wherein the second therapeutic agent is a chemotherapeutic drug for the treatment of breast cancer.
9. The method of claim 1, wherein the breast cancer comprises a breast carcinoma.

\* \* \* \* \*